US008657839B2

(12) United States Patent
To et al.

(10) Patent No.: US 8,657,839 B2
(45) Date of Patent: Feb. 25, 2014

(54) SYSTEMS AND METHODS FOR CABLE-BASED TISSUE REMOVAL

(71) Applicant: Spine View, Inc., Fremont, CA (US)

(72) Inventors: John T. To, Newark, CA (US); Gary Daniel Zaretzka, Castro Valley, CA (US); Hiep Nguyen, Milpitas, CA (US); Singfatt Chin, Pleasanton, CA (US); Robert May, Hayward, CA (US)

(*) Notice: Subject to any disclaimer, the term of this patent is extended or adjusted under 35 U.S.C. 154(b) by 0 days.

(21) Appl. No.: 13/731,733

(22) Filed: Dec. 31, 2012

(65) Prior Publication Data

US 2013/0317505 A1    Nov. 28, 2013

Related U.S. Application Data

(63) Continuation of application No. 13/245,836, filed on Sep. 26, 2011, now Pat. No. 8,343,179, which is a continuation of application No. 12/509,356, filed on Jul. 24, 2009, now abandoned.

(60) Provisional application No. 61/083,857, filed on Jul. 25, 2008, provisional application No. 61/106,858, filed on Oct. 20, 2008, provisional application No. 61/223,343, filed on Jul. 6, 2009.

(51) Int. Cl.
*A61B 17/32* (2006.01)

(52) U.S. Cl.
USPC .......................................... 606/170; 607/122

(58) Field of Classification Search
USPC ............. 606/42, 159, 167, 170, 180; 607/122
See application file for complete search history.

(56) References Cited

U.S. PATENT DOCUMENTS 6,319,242 B1 * 11/2001 Patterson et al. ............. 604/508

* cited by examiner

*Primary Examiner* — Victor Nguyen
(74) *Attorney, Agent, or Firm* — Ross M. Carothers; Morrison & Foerster LLP

(57) ABSTRACT

Systems and methods for treating disc herniation include surgical and endoscopic access and removal of disc tissue. The tissue removal devices that may be used include flexible elongate members, such as a cable, that may be inserted into a vertebral disc and rotated to pulverize the disc material and facilitate its removal.

3 Claims, 23 Drawing Sheets

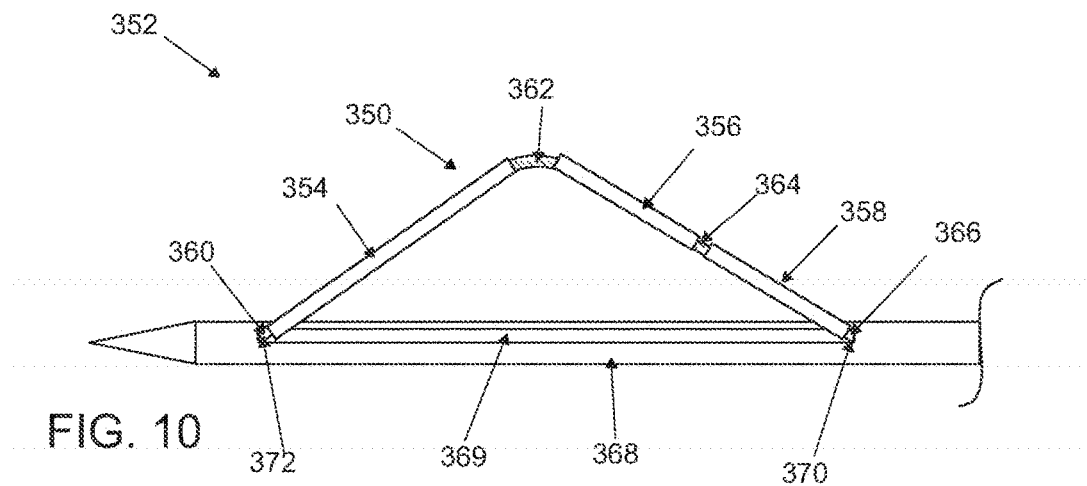
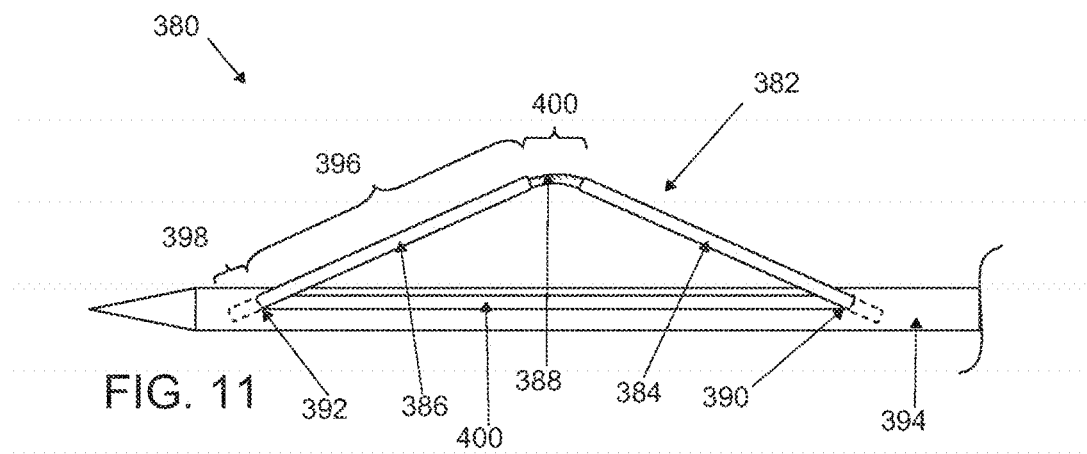

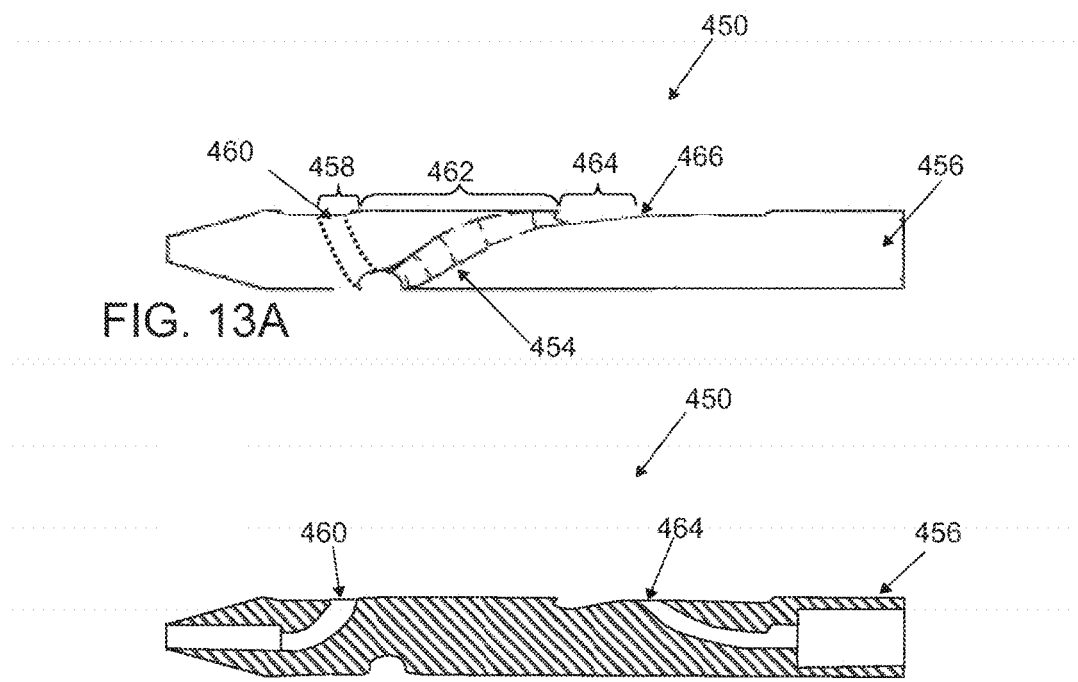
FIG. 13A
FIG. 13B
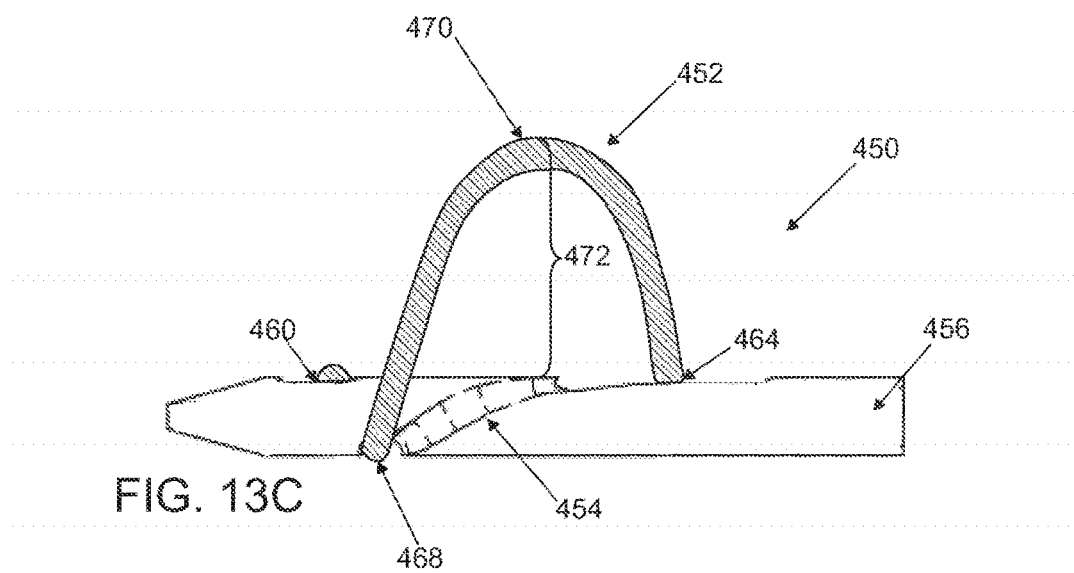
FIG. 13C

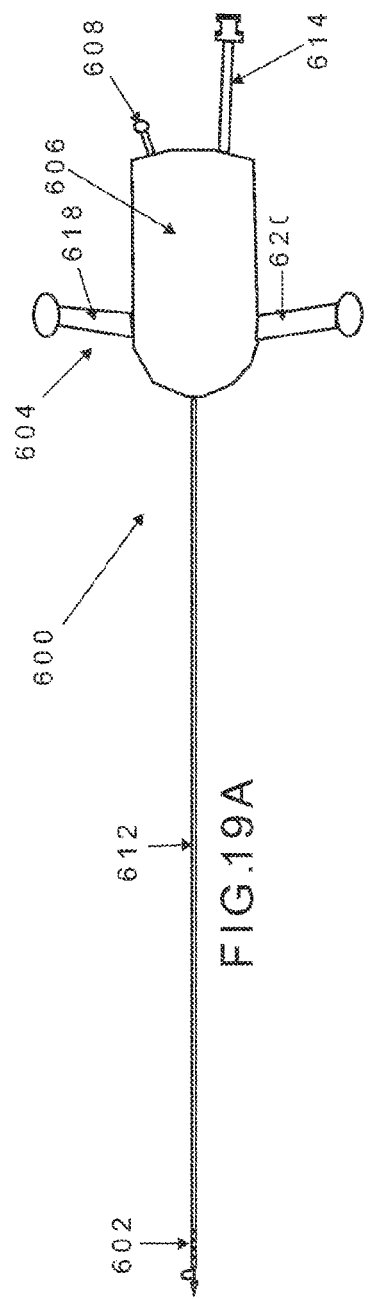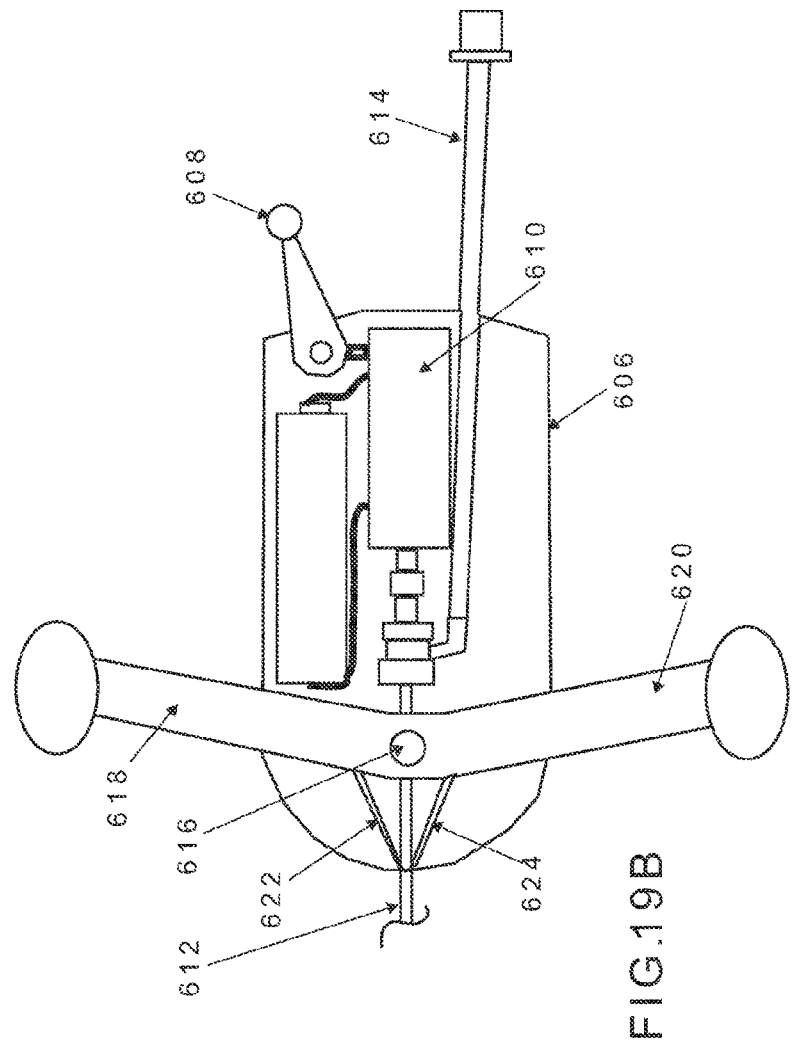
FIG.19A
FIG.19B

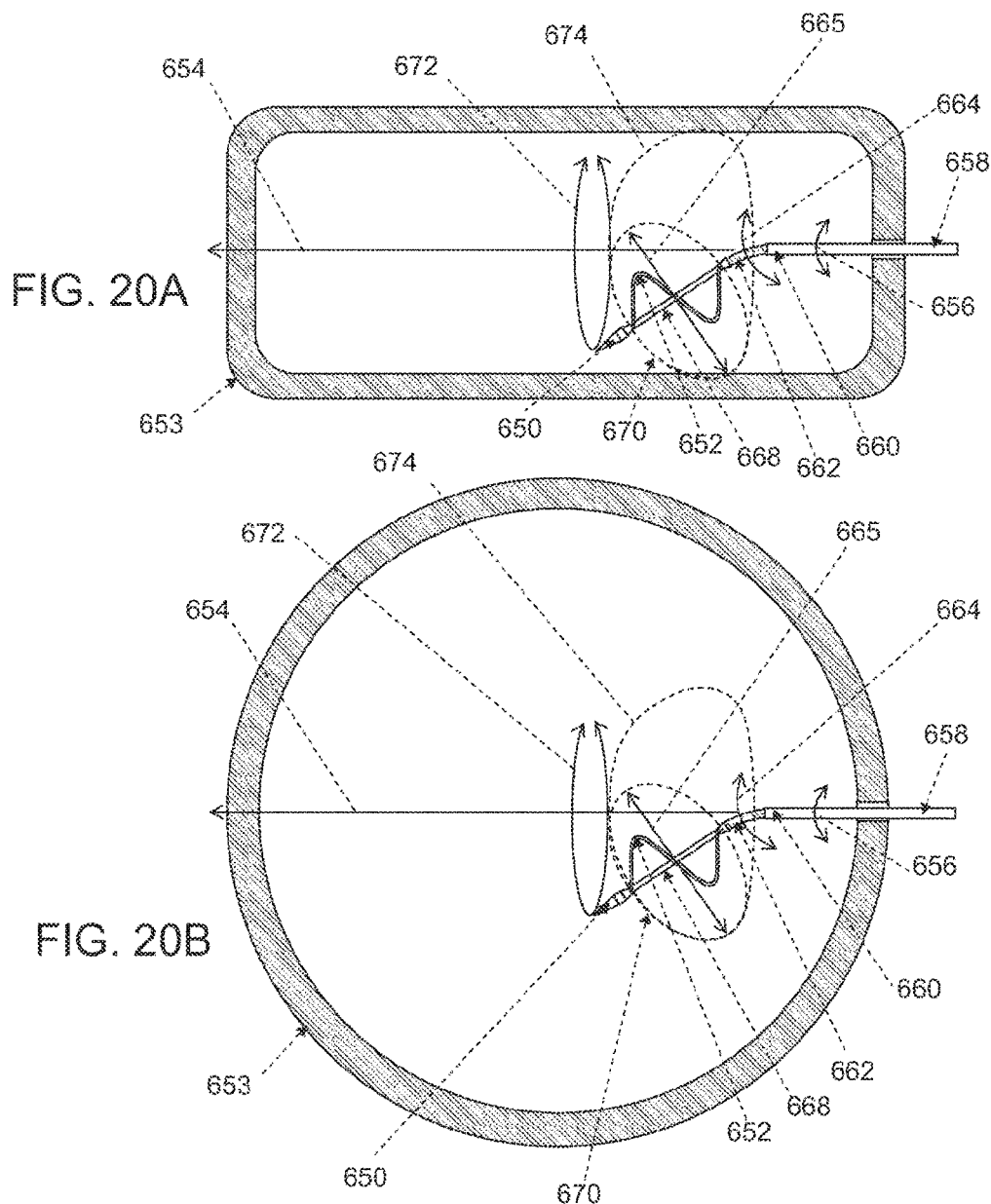

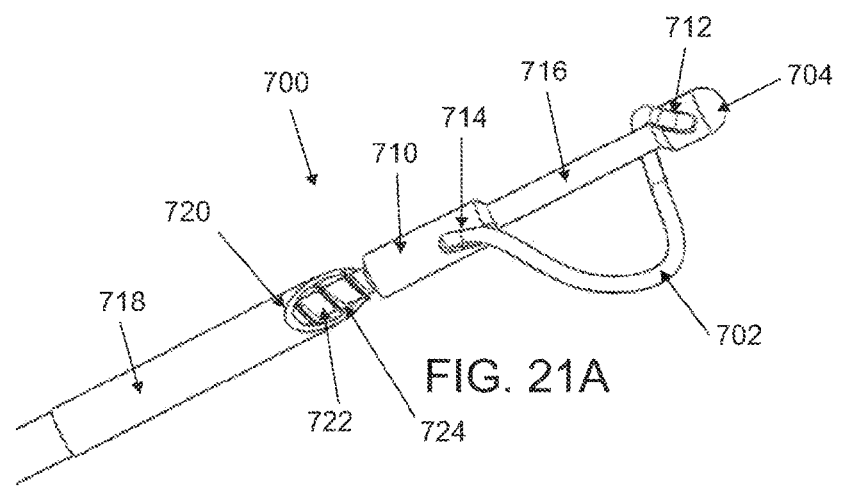
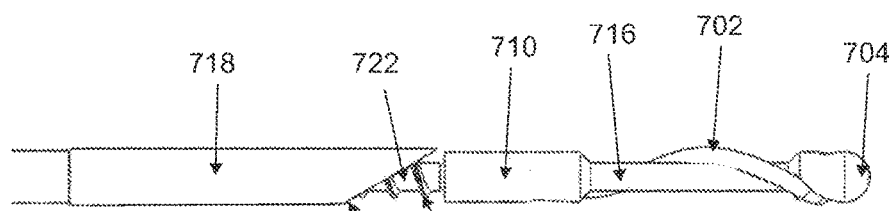
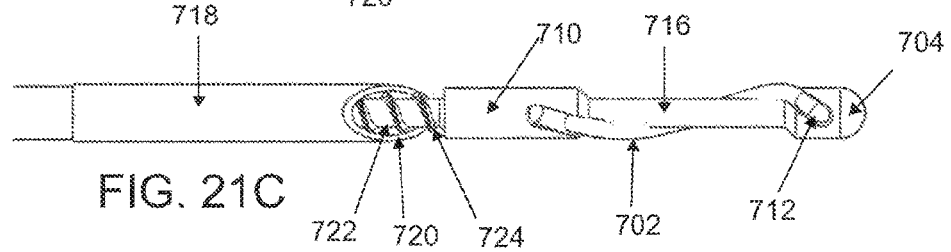
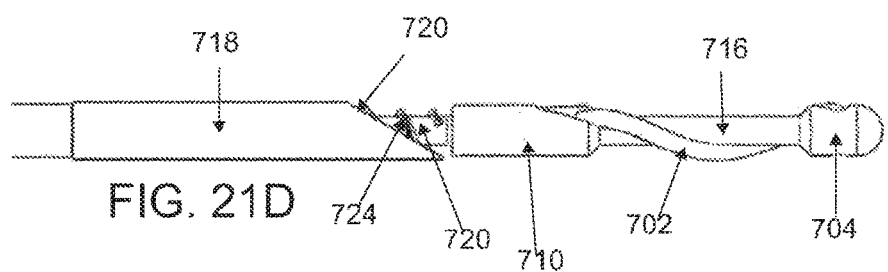

SYSTEMS AND METHODS FOR CABLE-BASED TISSUE REMOVAL

CROSS-REFERENCE TO RELATED APPLICATIONS

The application is a continuation of U.S. patent application Ser. No. 13/245,836, filed on Sep. 26, 2011, which is a continuation of U.S. patent application Ser. No. 12/509,356, filed on Jul. 24, 2009, which claims priority under 35 U.S.C. §119 (e) to U.S. Provisional Application No. 61/083,857 filed on Jul. 25, 2008, and U.S. Provisional Application No. 61/106,858 and was filed on Oct. 20, 2008, and Provisional Application No. 61/223,343 filed on Jul. 6, 2009, all of which are hereby incorporated by reference in their entirety.

BACKGROUND

Vertebral disc herniation is a common disorder where a portion of a vertebral disc, a cushion-like structure located between the bones of the spine, bulges out or extrudes beyond the usual margins of the disc and the spine. Disc herniation is believed to be the result of a loss of elasticity of the tissue comprising the disc, and is associated with increasing age. Disc herniation and other degenerative disc disease are also associated with spinal stenosis, a narrowing of the bony and ligamentous structures of the spine. Although disc herniation can occur anywhere along the perimeter of the disc, it occurs more frequently in the posterior and posterior-lateral regions of the disc, where the spinal cord and spinal nerve roots reside. Compression of these neural structures can lead to pain, parasthesias, weakness, urine and fecal incontinence and other neurological symptoms that can substantially impact basic daily activities and quality of life.

Temporary relief of the pain associated with disc herniation is often sought through conservative therapy, which includes positional therapy (e.g. sitting or bending forward to reduce pressure on spine), physical therapy, and drug therapy to reduce pain and inflammation. When conservative therapy fails to resolve a patient's symptoms, surgery may be considered to treat the structural source of the symptoms. Surgical treatments for disc herniation traditionally involve open procedures that require extensive dissection of muscle, connective tissue and bone along a patient's back to achieve adequate surgical exposure. These surgeries also expose the patient to a significant risk of complications, due to the presence of critical neurovascular structures near the surgical site. For example, a discectomy procedure may be used to decompress the herniation by accessing the affected disc and removing a portion of the disc and any loose disc fragments. To achieve sufficient access to the affected disc, a portion of the lamina or bony arch of the vertebrae may be removed, thereby increasing the invasiveness of the procedure. When discectomy fails to resolve a patient's symptoms, more drastic measures may include disc replacement surgery or vertebral fusion.

Fractures of the vertebrae bodies are another common disorder of the spinal column. When a vertebra fractures, the usual shape of the bone becomes compressed and distorted, which results in pain. These vertebral compression fractures (VCF), which may involve the collapse of one or more vertebrae in the spine, are a common finding and result of osteoporosis. Osteoporosis is a disorder that often becomes more severe with age and results in a loss of normal bone density, mass and strength. Osteoporosis often leads to a condition in which bones are increasingly porous or full of small holes and vulnerable to breaking. In addition to osteoporosis, vertebrae can also become weakened by cancer or infection.

In some instances, fractures of the vertebral bodies may be treated with surgical removal of the vertebral body and the implantation of a vertebral body replacement device. Other treatments may include vertebroplasty and kyphoplasty, which are minimally invasive procedures for treating vertebral compression fractures. In vertebroplasty, physicians use image guidance to inject a cement mixture through a hollow needle into the fractured bone. In kyphoplasty, a balloon is first inserted through the needle into the fractured vertebral body to restore at least some of the height and shape of the vertebral body, followed by removal of the balloon cement injection into the cavity formed by the balloon.

BRIEF SUMMARY OF THE INVENTION

Systems and methods for treating disc herniation include surgical and endoscopic access and removal of disc tissue. The tissue removal devices that may be used include flexible elongate members, such as a cable, which may be inserted into a vertebral disc and rotated to pulverize the disc material and to facilitate its removal.

In one example, a tissue removal system is provided, comprising a handheld housing with a power supply, an adjustment assembly and a motor configured to rotate at a speed of at least about 7000 rpm, an outer shaft attached to the handheld housing and having a length of about 10 cm to about 30 cm and an average diameter of less than about 2 mm, an inner shaft located within the outer shaft and coupled to the motor, a tissue removal assembly comprising a tubular core attached to the inner shaft and comprising a distal side opening and a proximal side opening spaced about 10 mm or less from the distal side opening, and a single flexible multi-filament cable coupled to the adjustment assembly and comprising a distal section coupled to the distal side opening of the tubular core, a proximal section coupled to the proximal side opening, and a middle section therebetween located outside of the tubular core, wherein the single flexible multi-filament cable has a retracted configuration and an extended configuration wherein the perpendicular distance between the middle section of the single flexible multi-filament cable and the tubular core is at least about twice the average diameter of the tubular core. The average diameter of the outer shaft may be less than about 1 mm and/or the average diameter of the tubular core may be less than about 1 mm. In some variations, at least a portion of the multi-filament cable may be extended to a perpendicular distance of at least about 3 mm or about 5 mm with respect to the tubular core. The single flexible multi-filament cable may have a helical configuration, which may be right-handed or left-handed helical configuration, as well as a variable pitch configuration. The single flexible multi-filament cable may interconnect a proximal and a distal linear rigid rod. and the proximal linear rigid rod may be partially located in the proximal side opening and the distal linear rigid rod may be partially located in the distal side opening. In other variations, the cable may be coated or fused with a rigid polymer coating proximally and/or distally, or completely. The coating may be a polyimide coating. In some further examples, the tissue removal system may further comprise a steering assembly. The steering assembly may comprise a steering wire distally coupled to a flexible region of the outer shaft.

In another example, a system for tissue removal is provided, comprising a motor configured to rotate at a speed of at least 1000 rpm, a rotatable shaft assembly coupled to the motor, wherein the rotatable shaft assembly comprises a distal coupling site and a proximal coupling site comprising a proximal surface opening, and a flexible elongate member, comprising a distal section coupled to the distal coupling site of the rotatable shaft assembly and a proximal section slidably positioned in the proximal surface opening, and a middle section therebetween, wherein the flexible elongate member has a retracted configuration and an extended configuration wherein a perpendicular distance between the middle section of the flexible elongate member and the rotatable shaft assembly is greater in the extended configuration than in the retracted configuration. The flexible elongate member may comprise a flexible multi-filament elongate member, and in some but not all variations, the flexible multi-filament elongate member may comprise no more than about ten filaments. The proximal surface opening and the distal surface opening may be longitudinally aligned along the shaft or may be longitudinally offset, and may optionally further comprises a groove between the proximal surface opening and the distal surface opening. The groove may be straight or may be a helical groove, with a constant or a variable pitch. The rotatable shaft assembly may also further comprise a narrow segment located between the proximal surface opening and the distal surface opening. In some variations, the perpendicular distance between the middle section of the flexible elongate member and the rotatable shaft assembly in the extended configuration may be equal to or greater than about the average diameter of the rotatable shaft assembly, and sometimes may be equal to greater than about twice the average diameter of the rotatable shaft assembly. The rotatable shaft assembly may also comprise a distal penetrating tip. In some variations, the length of the flexible elongate member outside of the rotatable shaft assembly may be different in the retracted configuration and the extended configuration. The distance between the distal coupling site and the proximal surface opening may be unchanged in the retracted configuration and the extended configuration. The flexible elongate member may also comprise at least one rigid section and at least one flexible section, and in some examples, may comprise at least two rigid sections, which may be interconnected by a flexible cable. At least one rigid section may be a linear rigid section. In some variations, the proximal rigid rod may be located in the proximal surface opening. The proximal rigid rod may also be located in the proximal surface opening when the flexible elongate member is in the extended configuration. In some examples, at least a portion of the flexible elongate member may comprise a grit surface with an average grit number in the range of about 200 to about 500. The flexible elongate member may have a flexural modulus that is less than a flexural modulus of intact bony tissue, and/or less than a flexural modulus of intact annular fibrosis tissue. In some variations, the flexible elongate member may have a generally uniform flexural modulus along its length. In some systems, the rotatable shaft assembly may be coupled to the motor by a bendable driveshaft. The system may also further comprise a steering assembly configured to bend the driveshaft. In some examples, the ratio of the perpendicular distance between the middle section of the flexible elongate member and the rotatable shaft assembly in the extended configuration to a diameter of the rotatable shaft assembly may be at least about 3:1 or at least about 5:1. The flexible elongate member may comprise a polymeric coating, which may or may not comprise polyimide.

In another embodiment, a method for treating a patient is provided, comprising inserting a cable toward a vertebral tissue region, wherein the cable is coupled to a rotatable shaft assembly, extending the cable from an opening of the rotatable shaft assembly, rotating the cable around a cable rotation axis of the rotatable shaft assembly, and withdrawing the cable from the patient. The method may further comprise retracting the cable into the opening of the rotatable shaft assembly, pulverizing vertebral tissue rotating the cable, removing the pulverized vertebral tissue from the patient, and/or removing the pulverized vertebral tissue comprises suctioning vertebral tissue. Rotating the cable may comprise rotating the cable to a speed of at least about 1000 rpm or about 5000 rpm or greater. The method may further comprise providing access to the vertebral tissue region using a cannula and/or using a surgical retractor. The vertebral tissue may comprise vertebral bone tissue and/or vertebral disc tissue and may further comprise penetrating vertebral disc tissue with a distal tip of the rotatable shaft assembly or another instrument. The vertebral disc tissue may be located within the annulus fibrosus of a vertebral disc, or may include the annulus. In some examples, penetrating the vertebral disc may comprise forming a self-sealing passageway through the wall of the vertebral disc, which may be less than about 2 mm or even less than about 1 mm in size. The may further comprise positioning the cable within the vertebral disc, and sometimes extending the cable may be performed while at least a portion of the cable is in the vertebral disc. Extending the cable may also be performed while at least a portion of the cable is in a nucleus pulposus of the vertebral disc. Extending the cable may also be performed while at least a portion of the cable is in a bony structure adjacent to the vertebral disc. Pulverizing vertebral tissue may comprise pulverizing nucleus pulposus tissue, and may be performed without substantially damaging annulus fibrosus tissue and/or bony endplate tissue of an adjacent vertebral body. In some examples, the method may further comprise bending the rotatable shaft assembly, and rotating the cable may be performed while the rotatable shaft assembly is bent. The method may also further comprise rotating a proximal segment of the rotatable shaft assembly about a proximal rotation axis that is different from the cable rotation axis of the rotatable shaft assembly. Rotating the cable around the cable rotation axis of the rotatable shaft assembly may occur while the rotatable shaft assembly is rotating about the proximal rotation axis. Extending the cable may comprise extending a portion of the cable to a separation distance of at least about 3 mm from the rotatable shaft assembly, or at least about 5 mm from the rotatable shaft assembly. Pulverizing vertebral tissue about the cable may be performed in a tissue zone that has a diameter with respect to the rotatable shaft assembly that is at least about 5 times greater than a diameter of the rotatable shaft assembly, or sometimes is at least about 7 times greater than a diameter of the rotatable shaft assembly.

In another embodiment, a method for treating disc herniation is provided, comprising endoscopically visualizing a disc herniation, inserting an tissue removal device into vertebral disc tissue, wherein the tissue removal device comprises an elongate shaft with a distal shaft segment coupled to an adjustable pulverizing member, bending the elongate shaft of the tissue removal device toward a target site within the vertebral disc tissue, setting the adjustable pulverizing member to a first distance from the distal shaft segment, mechanically pulverizing the vertebral disc tissue located at about the first distance, endoscopically visualizing the disc herniation after pulverizing the vertebral disc tissue located at the first distance, adjusting the adjustable pulverizing member to a second distance from the distal shaft segment that is greater than the first distance, mechanically pulverizing vertebral disc tissue located about the second distance, and endoscopically visualizing the disc herniation after pulverizing the vertebral disc tissue located at the second distance. The may further comprise unbending the elongate shaft, and withdrawing the elongate shaft from the vertebral disc tissue.

BRIEF DESCRIPTION OF THE DRAWINGS

FIG. 10 depicts one embodiment of a tissue removal device with a plurality of rigid supports;

FIG. 11 depicts another embodiment of a tissue removal device with rigid supports;

FIGS. 13A and 13B are side elevational and longitudinal cross-sectional views of another embodiment of a tissue removal device; FIG. 13C is a side elevational view of the tissue removal device of FIG. 13A with a tissue-removing cable in an extended state;

FIG. 19A schematically depicts one embodiment of a flexible tissue removal device; FIG. 19B is a schematic side elevational view of the proximal end of the flexible tissue removal device of FIG. 19A with a portion of the housing removed; FIGS. 20A and 20B are schematic side and superior cross-sectional views of a steerable tissue removal device inserted into a vertebral disc, respectively.

FIG. 21A depicts the distal end of another embodiment of a tissue removal device with a blunt tip and in an extended configuration; FIGS. 21B to 21D depict various views of the tissue removal device in FIG. 21A in the retracted configuration.

DETAILED DESCRIPTION OF THE INVENTION

Figure 1:
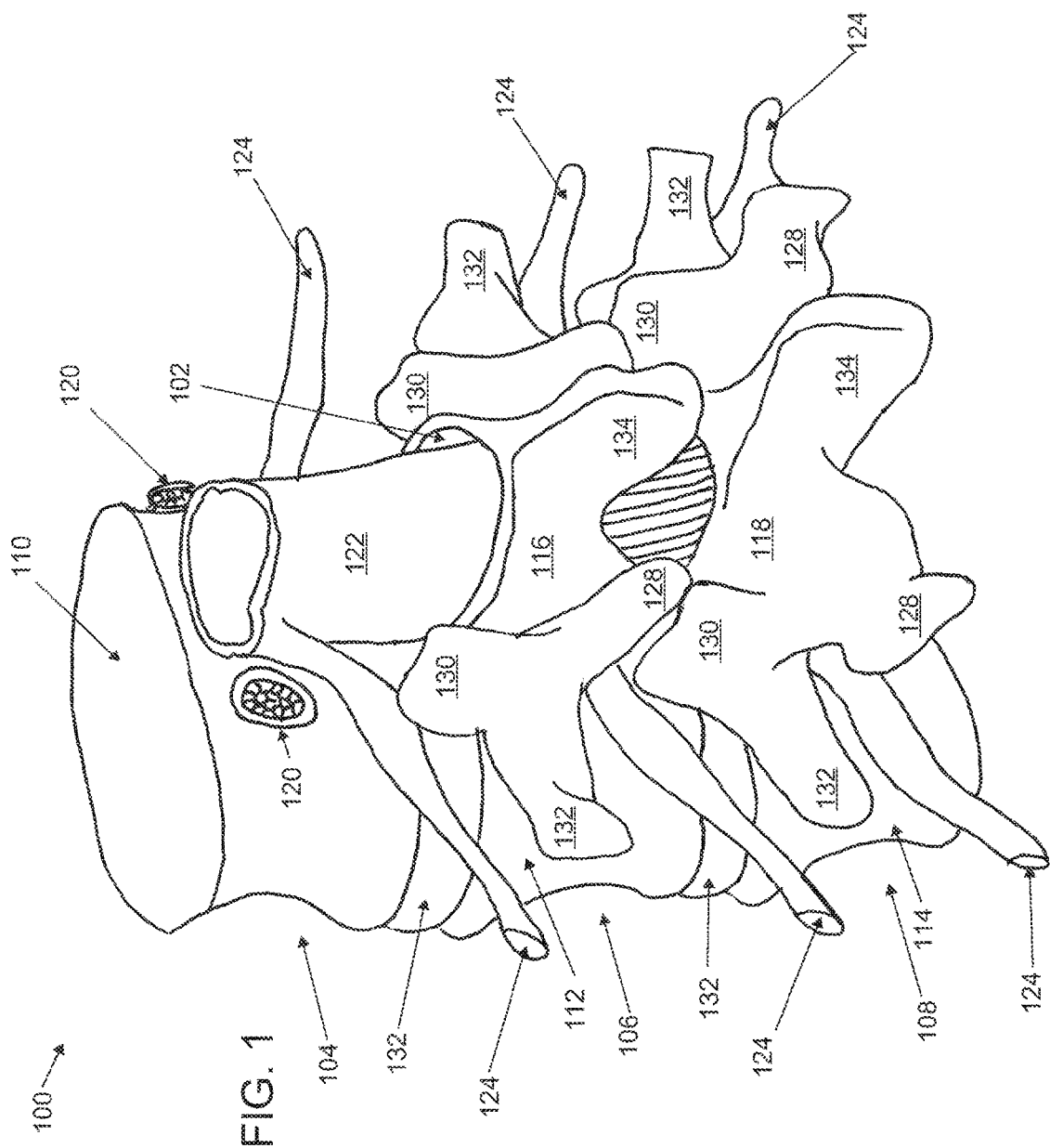
FIG. 1 is a schematic perspective view of a portion of a lumbar spine.
Figure 2:
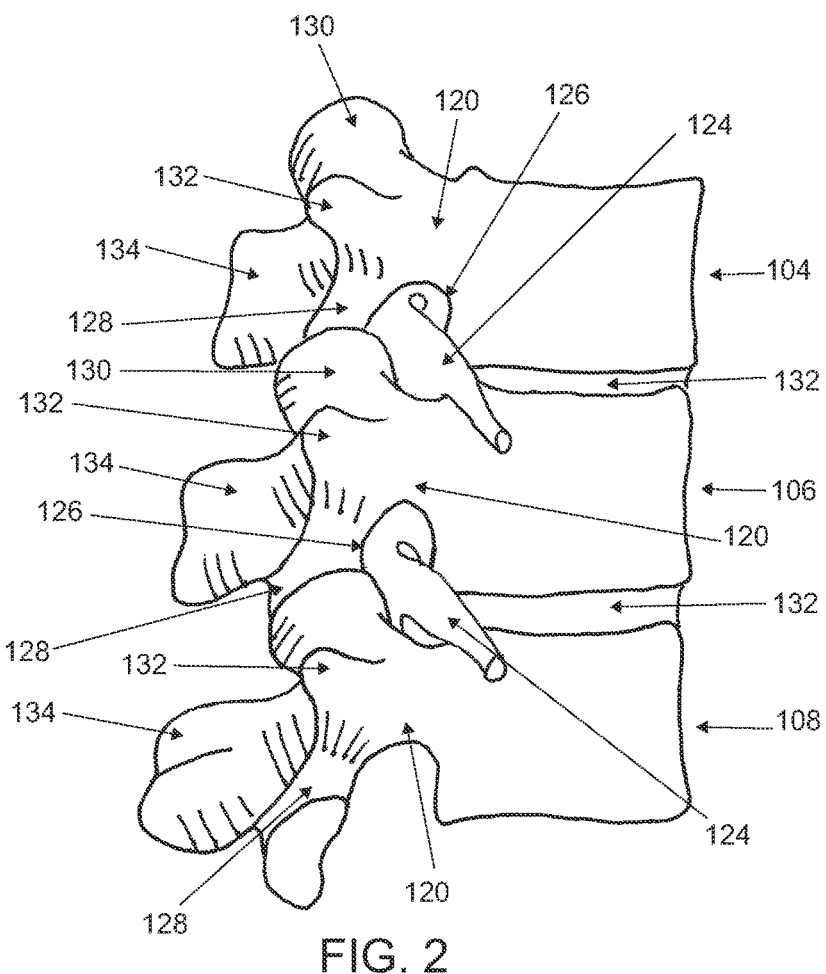
FIG. 2 is a schematic side elevational view of a portion of the lumbar spine.

FIGS. 1 and 2 are schematic views of a lumbar region of a spine 100. The vertebral canal 102 is formed by a plurality of vertebrae 104, 106, and 108, which comprise vertebral bodies 110, 112 and 114 anteriorly and vertebral arches 116 and 118 posteriorly. The vertebral arch and adjacent connective tissue of the superior vertebra 104 has been omitted in FIG. 1 to better illustrate the spinal cord 122 within the vertebral canal 102. Spinal nerves 124 branch from the spinal cord 122 bilaterally and exit the vertebral canal 102 through intervertebral foramina 126 (seen best in FIGS. 2 and 3) that are formed by the adjacent vertebra 104, 106 and 108. The intervertebral foramina 126 are typically bordered by the inferior surface of the pedicles 120, a portion of the vertebral bodies 104, 106 and 108, the inferior articular processes 128, and the superior articular processes 130 of the adjacent vertebrae. Also projecting from the vertebral arches 116 and 118 are the transverse processes 132 and the posterior spinous processes 134 of the vertebrae 106 and 108. Located between the vertebral bodies 110, 112 and 114 are the vertebral discs 132.

Figure 3:
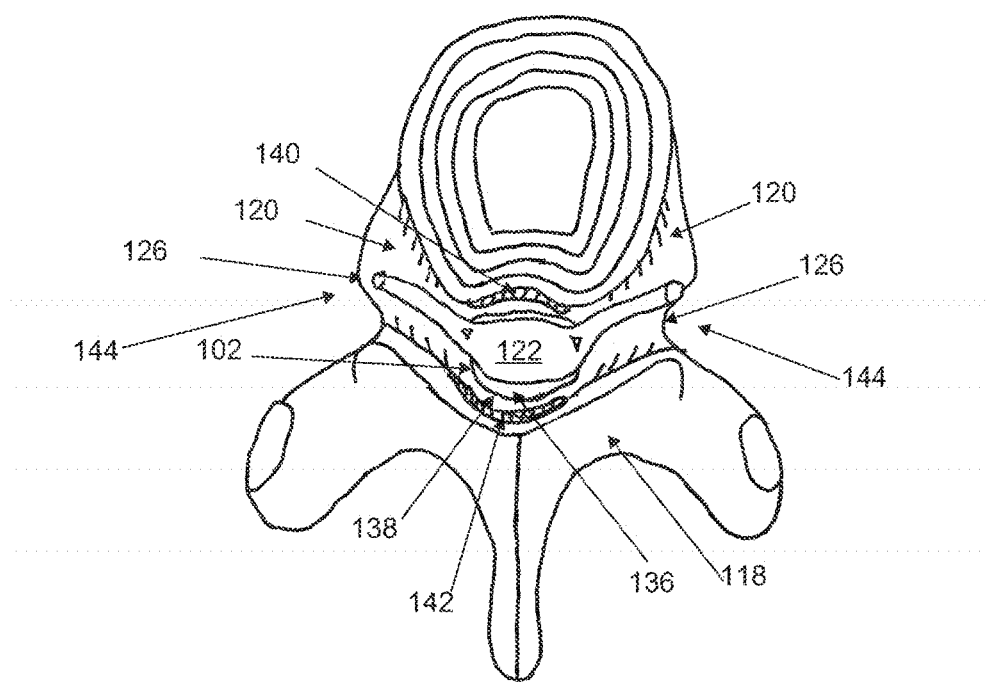
FIG. 3 is a schematic superior view of a portion of a lumbar vertebra and disc.

Referring to FIG. 3, the spinal cord 122 is covered by a thecal sac 136. The space between the thecal sac 136 and the borders of the vertebral canal 102 is known as the epidural space 138. The epidural space 138 is bound anteriorly and posteriorly by the longitudinal ligament 140 and the ligamentum flavum 142 of the vertebral canal 102, respectively, and laterally by the pedicles 120 of the vertebral arches 116 and 118 and the intervertebral foramina 126. The epidural space 138 is contiguous with the paravertebral space 144 via the intervertebral foramina 126.

Figure 4A:
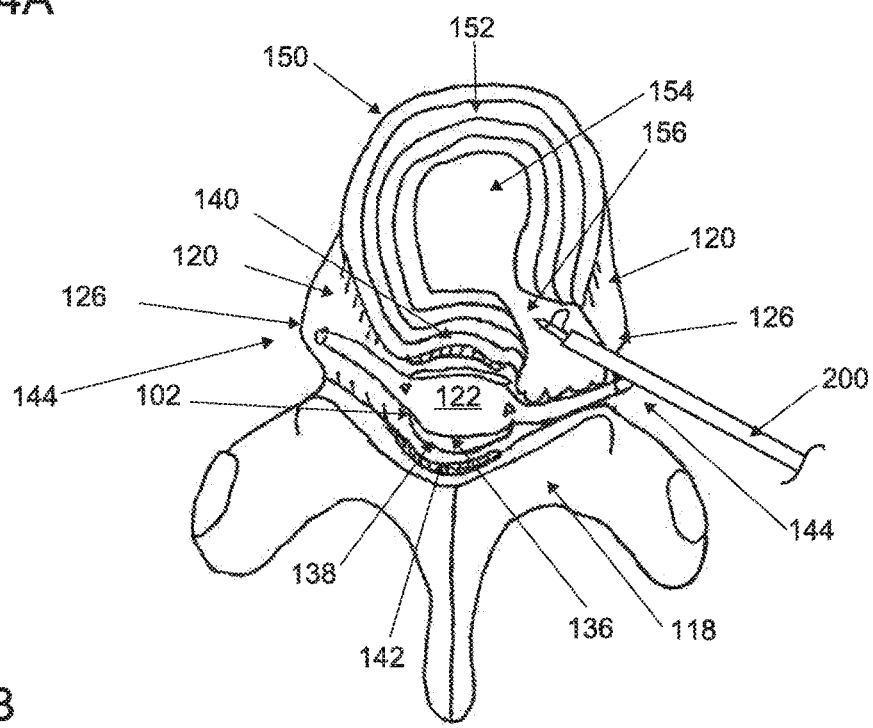
FIGS. 4A and 4B are schematic superior views of a herniated disc during and after treatment, respectively.

Referring to FIG. 4A, a vertebral disc 150 typically comprises an outer, multi-layer, annular band of connective tissue, known as the annulus fibrosus 152, which encases a gel-like resilient material known as the nucleus pulposus 154. The nucleus pulposus 154 acts as a shock-absorbing structure for the forces acting on the spine. Both the annulus fibrosus 152 and the nucleus pulposus 154 are elastic collagenous structures which, over time, may decrease in elasticity and cause the nucleus pulposus to bulge out at a weakened region of the annulus fibrosus 152, and even extrude through the annulus fibrosus 152. FIG. 4A schematically depicts an extrusion 156 of the nucleus pulposus 154, which has penetrated through the wall of the annulus fibrosus 152 within an intervertebral foramen 126 and compressed a nerve 124 exiting the spine. Although the extrusion 156 remains in continuity with the remaining nucleus pulposus 154, the extrusion 156 may sometimes pinch off or separate, resulting in the sequestration of a portion of the nucleus.

Figure 4B:
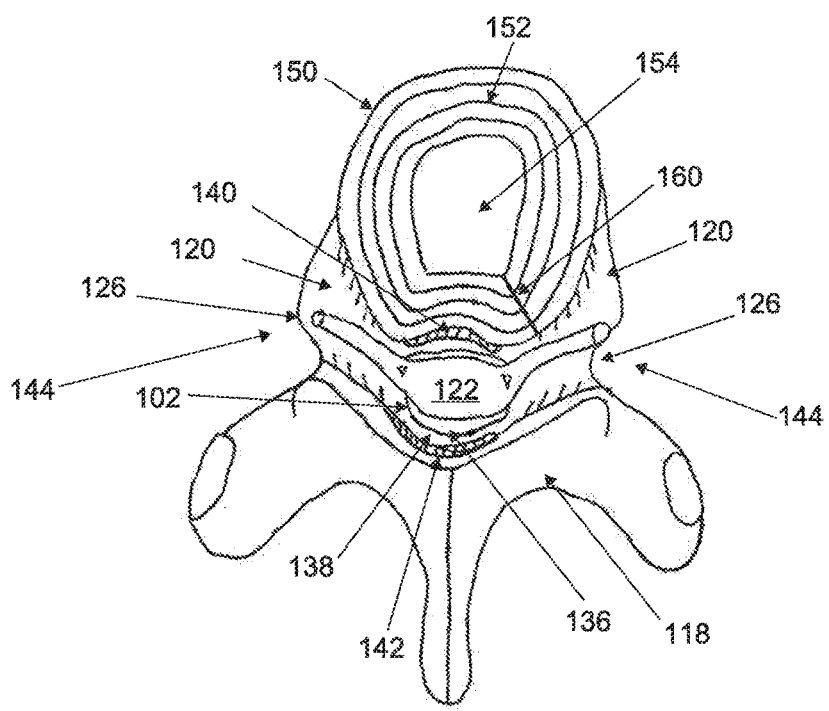

As mentioned previously, treatments of disc herniation may involve internal access to the affected disc with removal or volume reduction of the disc material. This may relieve the pressure causing the bulging or extrusion to at least partially restore the profile of the disc. In FIG. 4A, for example, a tissue removal device 200 has been inserted into the extrusion 156 extending out of the herniated disc 150. The tissue removal device 200 is then actuated to break up and remove the extruded material. In some embodiments, the tissue removal device 200 may be further inserted distally into the disc 150. Additional tissue with the disc 150 may then be removed. As shown in FIG. 4B, after removing a volume of the nucleus pulposus 154 and relieving some of the pressure causing the extrusion 156, the extrusion 156 was able to retract back into the disc 150, thereby reducing the extrusion pathway 160 and relieving compression of the spinal nerve 124. Although contralateral access of the herniated disc is depicted in FIG. 4A, ipsilateral access may also be used. Furthermore, direct tissue removal of the extruded herniated disc may also be performed.

Devices used to remove disc tissue for discectomy or nucleotomy may include lasers, discectomes, trephines, burrs, rongeurs, rasps, curettes and cutting forceps. Many of these devices have a substantial cross-sectional size, and when inserted into a disc, create an insertion channel which substantially compromises the integrity of the annulus fibrosus at the insertion site. Thus, any remaining nucleus pulposus material may extrude or herniate through the insertion site without taking measures to suture or otherwise close the insertion site, thereby adding complexity to the discectomy or nucleotomy procedure.

Figure 5A:
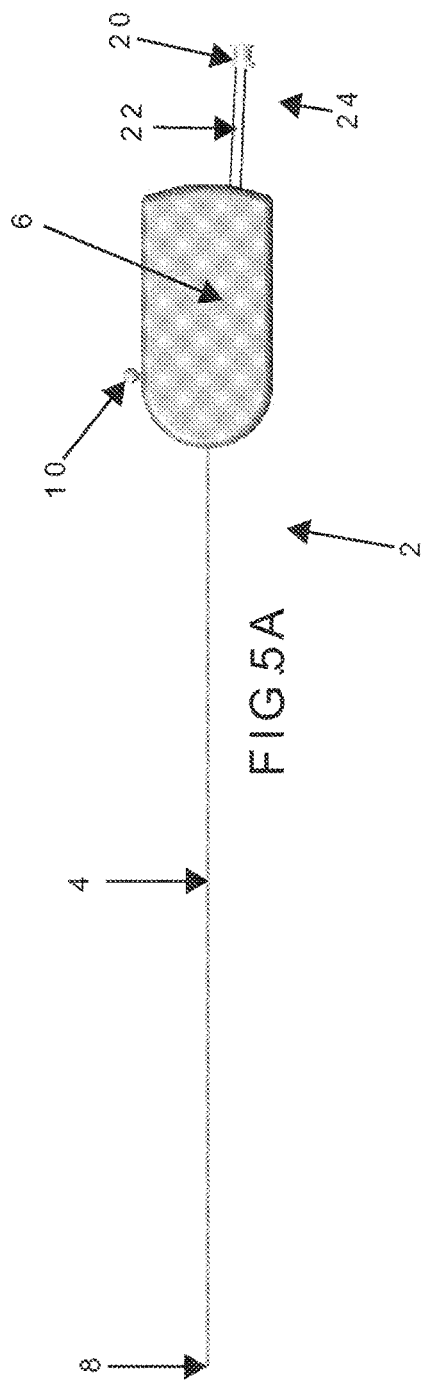
FIG. 5A is a side elevational view of an embodiment of a tissue removal device.

In contrast, a tissue removal device may be configured for minimally invasive insertion toward or into a vertebral disc without requiring suturing, gluing or other procedures to seal or close the access pathway into the disc. The tissue removal device may be used for any of a variety of procedures, including but not limited to discectomy, nucleotomy, lysis of adhesions, and other tissue removal procedures in the spine and throughout other regions of the body. FIG. 5A depicts one embodiment of a tissue removal device 2, comprising an outer tube 4 coupled to a housing 6. The static outer tube 4 covers a rotating drive shaft (not shown) that is attached to a tissue removal assembly 8. In other embodiments, the tissue removal device 2 may lack an outer tube and the drive shaft of the tissue removal device may be inserted into a lumen of a cannula or other access device. The housing 6 contains one or more components configured to control the tissue removal assembly 8 and other optional features of the tissue removal device 2. The tissue removal assembly 8, examples of which are described in greater detail below, may be configured to cut, chop, grind, burr, pulverize, debride, debulk, emulsify, disrupt or otherwise remove tissue when rotated at various speeds. Emulsification includes, for example, forming a suspension of tissue particles in a medium, which may be the existing liquid at the target site, liquid added through the tissue removal device, and/or liquid generated by the debulking of the tissue. Optional components may include, but are not limited to, a motor configured to rotate or move the tissue removal assembly, a power source or power interface, a motor controller, a tissue transport assembly, an energy delivery or cryotherapy assembly, a therapeutic agent delivery assembly, a light source, and one or more fluid seals. The optional tissue transport assembly may comprise a suction assembly and/or a mechanical aspiration assembly. One or more of these components may act through the outer tube 4 to manipulate the tissue removal assembly and/or other components located distal to the housing 6, or from the housing 6 directly. For example, the tissue removal device 2 further comprises an optional port 20 that may be attached to an aspiration or suction source to facilitate transport of tissue or fluid out of the target site or patient. The suction source may be a powered vacuum pump, a wall suction outlet, or a syringe, for example.

The housing 6 may further comprise a control interface 10 that may be used to control the power state of the tissue removal device 2, including but not limited to on and off states. In this particular embodiment, the control interface 10 comprises a lever or pivot member, but in other embodiments, control interface 10 may comprise a push button, a slide, a dial or knob. In some embodiments, the control interface 10 may also change the motor speed and/or movement direction of the tissue removal assembly 8. A bi-directional tissue removal device may be provided, for example, as a potential safety feature should the tissue removal assembly 8 get lodged in a body tissue or structure. The web-like connective tissue that may be found in the epidural space may get wound onto or caught up on the burr device or other tissue removal device. This connective tissue may be dislodged with a bi-directional tissue removal device by reversing the direction of rotation to unwind the tissue. The control interface 10 may be analog or digital, and may comprise one or more detent positions to facilitate selection of one or more pre-selected settings. In other embodiments, a separate motor control interface may be provided for one or more features of the motor. In still other embodiments, control interfaces for other features of the tissue removal device may be provided.

Figure 5B:
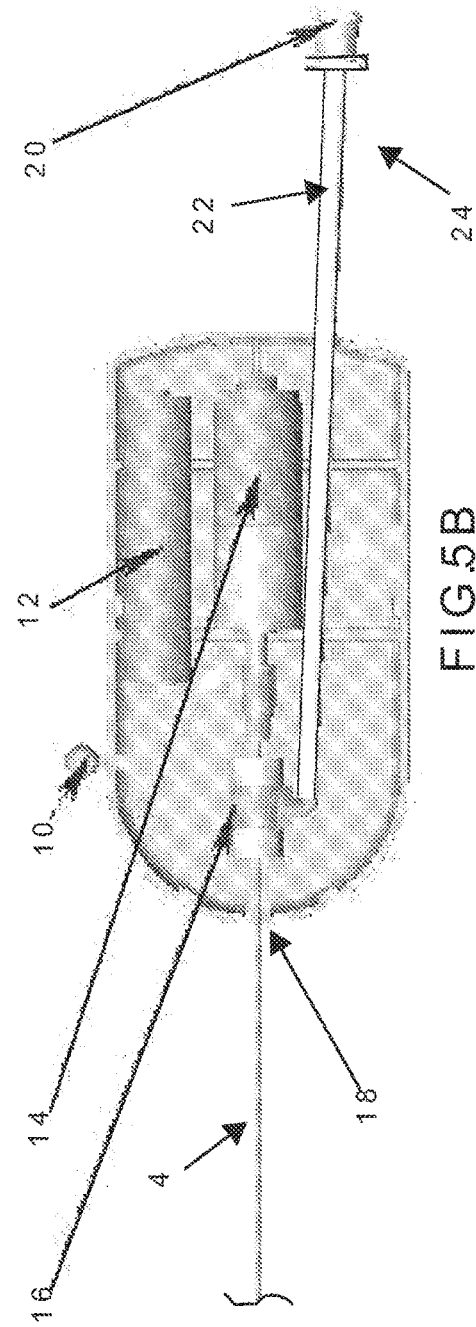
FIG. 5B is a detailed cutaway view of the device in FIG. 5A.
Figure 6A:
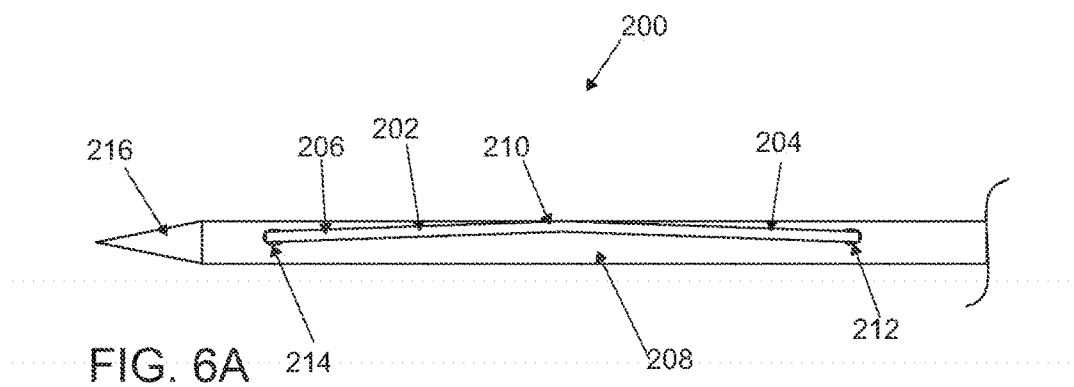
FIGS. 6A and 6B are side elevational views of an embodiment of tissue removal device with a rotatable elongate member in its retracted and extended configurations, respectively.
Figure 6B:
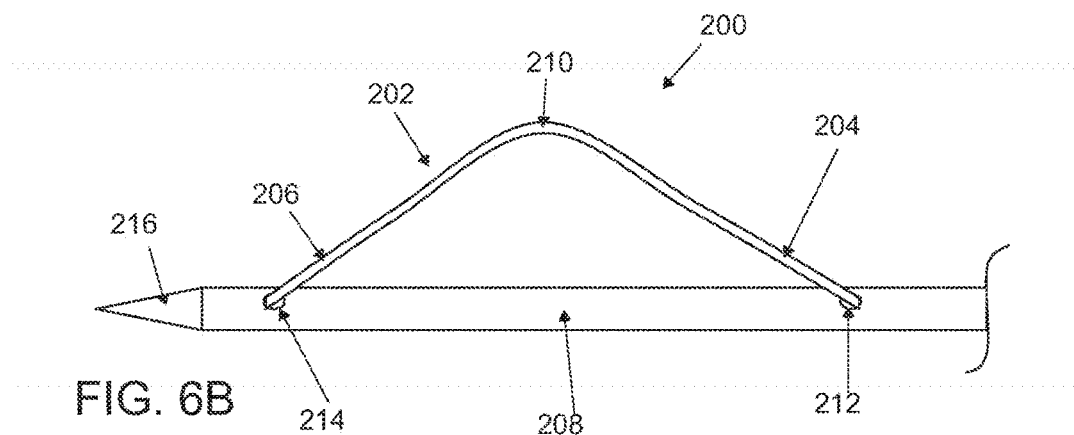

Referring to FIGS. 6A and 6B, the tissue removal assembly 200 may comprise at least one elongate member 202 having a proximal section 204 and distal section 206, with each section coupled to a rotatable shaft 208. The elongate member 202 has a retracted configuration, shown in FIG. 5A, and an extended configuration, shown in FIG. 5B. In the extended configuration, at least a portion 210 of the elongate member 202 is displaced farther away from the rotatable shaft 208 than the same portion 210 in the retracted configuration. To adjust the configuration of the elongate member 202, the proximal section 204 of the elongate member 202 may be slid in or out of a proximal opening 212 of the rotatable shaft 208 to alter the exposed length of the elongate member 208 between the proximal opening 212 and a distal opening 214 (or distal attachment of the distal section 206) of the elongate member 202. The percentage change in the length of the elongate member 202 from its retracted configuration to its extended configuration may be in the range of about 10% to about 60% or more, sometimes about 20% to about 40%, and other times about 15% to about 20%. In some embodiments, transformation of the elongate member 202 between configurations may include sliding its distal section 206 in or out of the distal opening 214, in addition to or in lieu of movement between the proximal section 204 and the proximal opening 212.

The tissue removal device 200 may further comprise a distal head 216 with a conical configuration, as depicted in FIGS. 6A and 6B. Other head configurations are also contemplated, including but not limited to an ovoid configuration, a dome configuration, a concave configuration, a cube configuration, etc. The head 216 may be configured to penetrate or dissect body tissue, such as the annular wall of a vertebral disc, and may be used while the rotatable shaft 208 is being rotated, or when the rotatable shaft 208 is not rotated. In other embodiments, the head may comprise multiple points or edges that may be used to cut, chop, grind, burr, pulverize, debride, debulk, emulsify, disrupt or otherwise remove tissue or body structures. In still other embodiments, the head may comprise surfaces with a grit that may be used as a burr mechanism. The grit number may range from about 60 to about 1200 or more, sometimes about 100 to about 600, and other times about 200 to about 500.

The head may optionally comprise a port or aperture which may be used to perform suction or aspiration at the target site and/or to perfuse saline or other biocompatible fluids or materials to the target site. Use of saline or other cooling materials or liquids, for example, may be used to limit any thermal effect that may occur from frictional or other forces applied to the target site during removal procedures. The saline or other materials may or may not be chilled. In other embodiments, one or more therapeutic agents may be provided in the saline or fluid for any of a variety of therapeutic effects. These effects may include anti-inflammatory effects, anti-infective effects, anti-neoplastic effects, anti-proliferative effects, hemostatic effects, etc.

Figure 7:
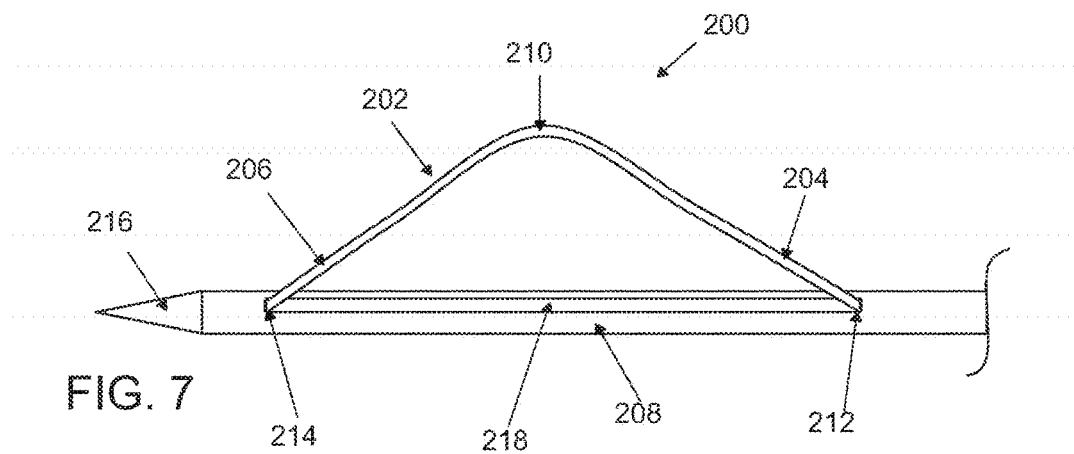
FIG. 7 depicts another embodiment of a tissue removal device with a recessed groove.

In some embodiments, the rotatable shaft may optionally comprise one or more recesses or grooves on its outer surface to receive the elongate member 202. For example, FIG. 7 depicts a single groove 218 between the proximal and distal openings 212 and 214 of the rotatable shaft 208. The depth and cross-sectional shape of the groove 218 may be configured to partially or fully receive the elongate member 202.

Figure 8:
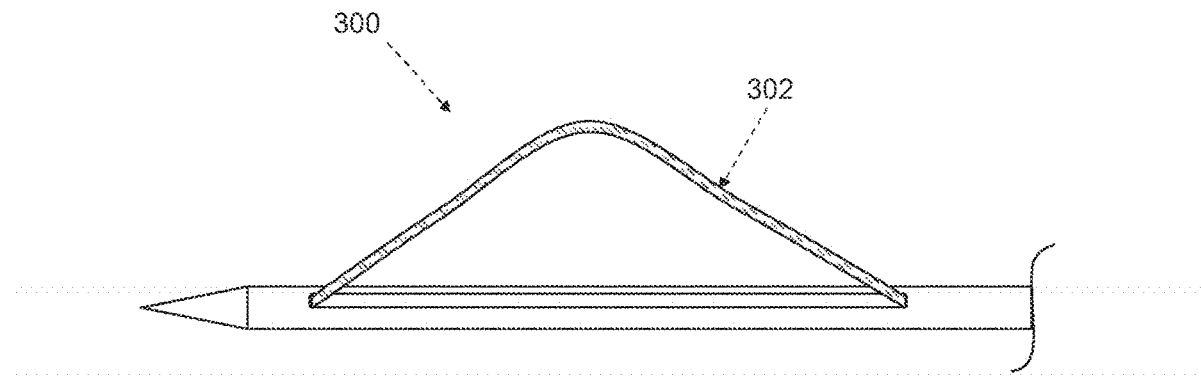
FIG. 8 depicts another embodiment of a tissue removal device with a multi-filament elongate member.

The elongate member 202 may comprise any of a variety of materials and structures. For example, the elongate member 202 may comprise titanium, a nickel-titanium alloy, stainless steel, a cobalt-chromium alloy, a polymer (e.g. nylon, polyester and polypropylene) or a combination thereof. The elongate member 202 may also have a monofilament or multi-filament structure. FIG. 8, for example depicts a tissue removal device 300 with an elongate member comprising a multi-filament cable 302. In some embodiments, a multi-filament elongate member may provide greater flexibility and/or stress tolerance than a monofilament elongate member. A multi-filament elongate member may comprise any number of filaments, from about 2 filaments to about 50 filaments or more, sometimes about 3 filaments to about 10 filaments, and other times about 5 filaments to about 7 filaments. In some embodiments, the elongate member has a flexural modulus that is less than the flexural modulus of bony tissue, such as the endplates of the vertebral bodies adjacent to a vertebral disc. In some instances, by providing a flexural modulus that is lower than certain body structures, damage to those body structures may be reduced or substantially eliminated. Thus, in some discectomy or nucleotomy procedures, a tissue removal device with an elongate member that has a flexural modulus that is less than the flexural modulus of both the bony tissue of the vertebral endplates and the flexural modulus of the annular fibrosus walls of the disc may be able to pulverize the inner tissue of a disc without damaging the adjacent walls of the disc or the vertebral bone. In some examples, the flexural modulus of the elongate member may be less than about half of the flexural modulus of intact bone or the annular fibrosis tissue, while in other embodiments, the flexural modulus of the elongate member is at least about 5 times lower, or even at least about 10 times or 20 times lower. In some embodiments, the flexural modulus of the elongate member is generally uniform along its exposed length or between its coupling sites on the rotatable shaft. For example, in some embodiments, the flexural modulus may not vary by more than about a 10× range along the length of the elongate member, while in other embodiments, the variation may be no greater than a range of about 5× or about 2×.

In some variations, the elongate member (e.g., multifilament or monofilament) of any of the variations described herein may be coated or sheathed with one or more materials. For example, the elongate member may be coated with polyimide, parylene, silicone, or urethane, or other polymer, or with an adhesive. The material may or may not penetrate into or between the filaments of a multi-filament elongate member. The coating may be applied by spray coating or dip coating, or other coating method, for example. In other examples, the material may be provided between the filaments but not on the exposed outer surfaces of the filaments, e.g. the material may be at least partially wiped or removed by air blowing from the outer surface of elongate member after spraying or dipping. In other variations, the coating material may comprise a sheath or tube that is glued or heat shrunk to the elongate member 202. In some variations, the sleeve or coating has an average thickness in the range of about 0.001 to about 0.01 inches, about 0.002 to about 0.008 inches, or about 0.003 to about 0.005 inches. The coating, sheath or tube may further comprise one or more support structures, such as a helical L304 stainless steel wire that is partially or completely embedded into the coating, sheath or tube, or adhered to the inner and/or outer surface of the coating, sheath or tube. The coating or sleeve may or may not cover the entire length of exposed or exposable elongate member or cable, and may also cover the unexposed portions of the elongate member or cable. In some variations, the coating or sleeve may be cover a portion of the proximal, middle, or distal portion of the elongate member and may be characterized as a percentage of coverage relative to the overall exposed or exposable length of the elongate member or cable, e.g. about 10%, about 20%, about 30%, about 40%, about 50%, about 60%, about 70%, about 80%, about 90%, or about 100%.

Although the elongate member 202 may have a retracted configuration and an extended configuration, the elongate member 202 may also have a native or base configuration in which the stress acting on the elongate member 202 is reduced compared to other configurations. This native configuration, if any, may be the retracted configuration, the extended configuration, or a configuration between the retracted configuration and the extended configuration. Thus, the stress exerted on the elongate member 202 in the native configuration may be lower in either the retracted configuration or the extended configuration, or a third configuration that is different from the retracted configuration or the extended configuration. In some embodiments, a native configuration that is similar to the extended configuration may be beneficial because a lower baseline stress acting on the elongate member 202 while in its extended configuration may provide greater stress tolerance from impacting tissues or bone before stressing the elongate member 202 beyond its fracture point. Although adjusting the elongate member 202 to its retracted configuration may result in greater stress acting on the elongate member 202, the stress may occur only during insertion and removal of tissue removal device 2, and without the impact stressed that act on the elongate member 202 during use. To produce the elongate member 202 with a particular native configuration, the manufacturing steps may vary depending upon the particular material or composition used. In embodiments where the elongate member 202 comprises stainless steel (e.g. 304L or 316L stainless steel) or nickel-titanium alloys, for example, a series of deformation steps and heat annealing steps may be used to form the elongate member 202 in a native, expanded configuration.

The elongate member 202 may have any of a variety of cross-sectional shapes, including but not limited to square, rectangular, trapezoidal, circular, elliptical, polygonal, and triangular shapes, for example. The cross-sectional shape and/or size may be uniform along its length, or may vary along one or more sections. In one example, the elongate member may have a tapered configuration, with a cross-sectional area that decreases from its proximal section to its distal section, or from its distal section to its proximal section. In some embodiments, the elongate member 202 may comprise a metallic wire or other elongate structure with a diameter or maximum cross-sectional dimension in the range of about 0.2 mm to about 1.5 mm or more, sometimes about 0.3 mm to about 1 mm, and other times about 0.3 mm to about 0.5 mm.

In some embodiments, the elongate member may be micropolished. Micropolishing may or may not reduce the risk of chipping or fragment formation when used to debride harder or denser body structures or tissues. In other embodiments, the elongate member may comprise a grit surface or a cutting edge along one or more portions of its length. For example, the elongate member may comprise a cutting edge with an edge angle in the range of about 90 degrees to about 10 degrees, sometimes about 75 degrees to about 15 degrees, and other times about 60 degrees to about 30 degrees, and still other times about 45 degrees to about 40 degrees. The configuration of the elongate member surface may be the same or different on opposing sides of the elongate member. For example, having different configuration on the leading surface compared to the trailing surface of the elongate member, may permit changes in the cutting, chopping, debriding, or emulsifying characteristics of the elongate member 202, depending upon its direction of rotation. In other embodiments, the leading and trailing surfaces may generally have the same features and may have similar performance in either rotation direction, but may also permit users to switch from one surface to the other if one surface has worn out. In still other embodiments, the rotation direction may be user-selected, depending upon the relative location of the tissue to be removed and any critical anatomical structures. For example, the rotation direction may be selected such that if the cutting edge 58 or 60 catches on the tissue or structure, tissue disrupting element 8 will be rotated away from the critical anatomical structure(s), if any.

Figure 9:
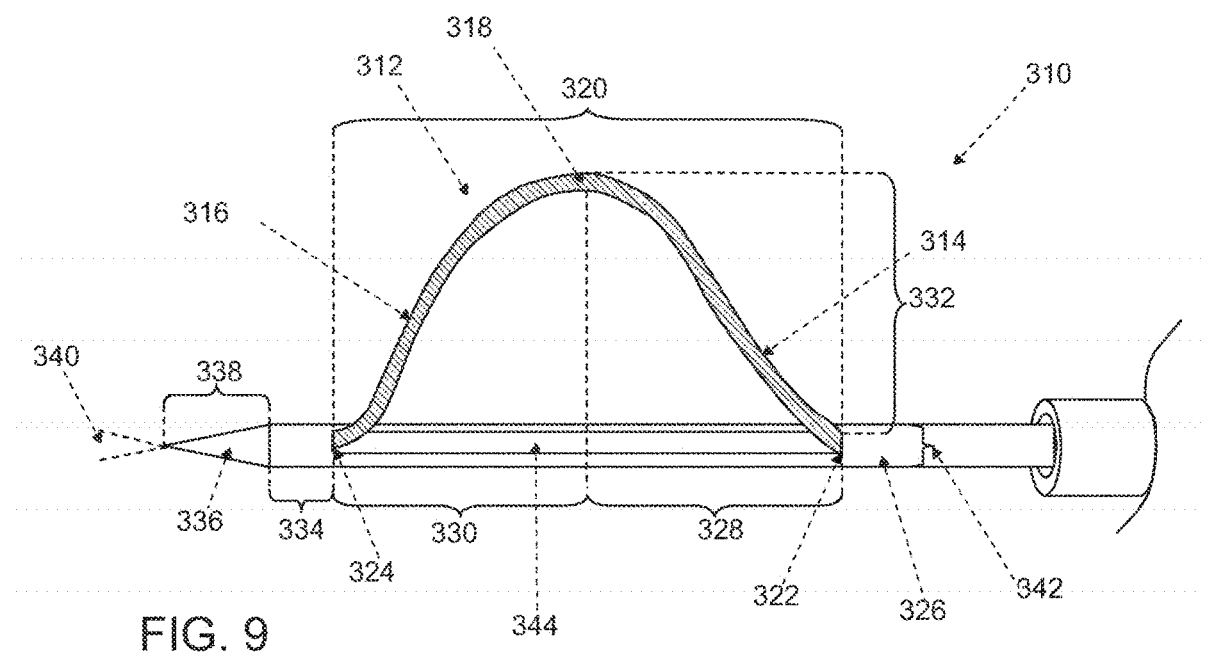
FIG. 9 depicts another embodiment of a tissue removal device.

As depicted in FIG. 6B, the elongate members 202 may have proximal and distal sections 204 and 206 with generally similar lengths and generally straight configurations, and a curved or angled middle portion 210 between them. FIG. 9, however, depicts another embodiment of a tissue removal device 310, comprising an elongate member 312 with proximal and distal sections 314 and 316 with concave configurations and a middle section 318 with a convex configuration. Other configurations are also contemplated, comprising any of a variety of linear, curved, or angled sections, and comprising symmetrical or asymmetrical configurations. In the embodiment depicted in FIG. 9, the longitudinal distance 320 between the proximal and distal openings 322 and 324 of the rotatable shaft 326 may be in the range of about 4 mm to about 30 mm or more, sometimes about 6 mm to about 15 mm, and other times about 9 mm to about 12 mm. The longitudinal distances 328 and 330 from the proximal and distal openings 322 and 324 to the peak displacement distance 332 of the elongate member 302, respectively, may be similar or different. In some embodiments, the distances 328 and 330 may be in the range of about 2 mm to about 20 mm or more, sometimes about 3 mm to about 10 mm, and other times about 4 mm to about 6 mm. The peak displacement distance 332 between the middle section 318 and the rotatable shaft 326 can vary, depending upon the particular configuration of the elongate member. The minimum displacement distance (not shown) of the middle section need not be zero, as in embodiments where the elongate member does not fully retract along its entire length against the rotatable shaft. In some embodiments, the displacement distance 318 may be in the range of about 2 mm to about 10 mm or more, sometimes about 3 mm to about 8 mm, and other times about 4 mm to about 6 mm. In some embodiments, the peak displacement distance 322 may be characterized relative to the longitudinal distance 320 or the proximal or distal distances 328 and 330 to the peak distance. For example, the ratio of the peak displacement distance to the longitudinal distance may be in the range of about 0.2 to about 1 or more, sometimes about 0.3 to about 0.8, and other times about 0.4 to about 0.5. The distance 334 between the distal opening 324 of the rotatable shaft and the distal head 336 may be in the range of about 0.5 mm to about 5 mm or more, sometimes about 1 mm to about 4 mm, and other times about 2 mm to about 3 mm. The length 338 of the head 336 may be in the range of about 2 mm to about 15 mm or more, sometimes about 3 mm to about 10 mm, and other times about 4 mm to about 5 mm. In embodiments comprising a conical or tapered head, the angle 340 of the head configuration may be in the range of about 10 degrees to about 90 degrees or more, sometimes about 20 degrees to about 60 degrees, and other times about 30 degrees to about 45 degrees.

The diameter 342 (or maximum transverse axial dimension) of the rotatable shaft 326 and/or head 336 may be in the range of about 0.5 mm to about 5 mm or more, sometimes about 1 mm to about 3 mm, and other times about 1 mm to about 2 mm. The diameter of the shaft 326 and the head 336 may be similar or different. The maximum cross-sectional dimension of the proximal and distal openings may be the same or different, and may be in the range of about 0.1 mm to about 1.5 mm or more, sometimes about 0.2 mm to about 1 mm, and other times about 0.4 mm to about 0.8 mm.

The width of the groove 344 of the rotatable shaft 326, if any, may be in the range of about 0.2 mm to about 1.5 mm or more, sometimes about 0.3 mm to about 1 mm, and other times about 0.4 mm to about 0.7 mm. The width of the groove 344 may also be characterized as a percentage of the diameter or width of the elongate member, which may be in the range of about 80% to about 400% or more, sometimes about 105% to about 300%, and other times about 150% to about 200%. As mentioned previously the depth of the groove 344 may be less than, similar to, or greater than the maximum transverse dimension of the elongate member 312. In some embodiments, the groove depth or average groove depth may be in the range of about 0.2 mm to about 2 mm or more, sometimes about 0.4 mm to about 1 mm, and other times about 0.6 mm to about 0.8 mm. In other embodiments, the depth of the groove may be a percentage of the depth of the elongate member, in the range of about 20% to about 200% or more, sometimes about 50% to about 125%, and other times about 40% to about 100%.

Although a single elongate member 202 is provided in the tissue removal device 200 depicted in FIG. 6A, other embodiments may comprise two or more elongate members. In some embodiments, however, a single elongate member may permit higher rotational speeds, due the reduced surface drag compared to tissue removal devices with multiple elongate members. In embodiments with multiple elongate members, the elongate members may be distributed uniformly or non-uniformly around the perimeter of the rotatable shaft. In some embodiments, each elongate member may have its own proximal and distal openings, but in other embodiments, two or more elongate members may share a proximal and/or distal opening. The proximal and/or distal openings may be located at the same or different longitudinal position on rotatable shaft, and each elongate member may have the same or different length or configuration. The elongate members may be independently adjustable or adjustable in groups.

Referring to FIG. 10, in some embodiments, the elongate member 350 of the tissue removal device 352 may comprise other structures 354, 356 and 358 attached or coupled to the flexible elongate member 350. These structures may comprise any of a variety of structures, including tubes, rods, bars, cutting discs or other cutting members, beads or other structures. In the specific example depicted in FIG. 10, the elongate member 352 comprises rigid sections 354, 356 and 358 alternating between flexible segments 360, 362, 364 and 366. One or more flexible segments may also be substituted with a mechanical joint, such as a pin joint or a hinge joint. In some embodiments, the flexible elongate segments 360, 362, 364 and 366 are part of a single contiguous flexible elongate member that passes through a lumen of each rigid section 354, 356 and 358 or are otherwise coupled to each rigid section 354, 356 and 358. In other embodiments, one or more of the flexible segments 360, 362, 364 and 366 are separate and interconnect only two rigid sections 354, 356 and 358 or a rigid section and the rotatable shaft 368 or a structure therein. The particular number, shape, flexibility/rigidity, lengths and locations of the rigid segments and flexible segments may vary and need not be uniform or symmetrical. In some embodiments, the percentage of rigid section to flexible section along the length of the fully extended elongate member may in the range of about 0 to about 99%, sometimes about 50% to about 95%, and other times about 75 to about 90%. In some embodiments, the length of the flexible segment may be less than about 75% of the length of the adjacent rigid segments, sometimes less than about 50%, and other times less than about 20% or about 10%.

In the example shown in FIG. 10, the tissue removal device 352 comprises one rigid section 354 that is larger than the other rigid sections 356 and 358. The section located at the peak displacement distance of the elongate member 350 may be a flexible segment 362 as shown in FIG. 10, or a rigid section in other embodiments. The rigid sections 354, 356 and 358 are generally linear in shape, but may also be curved or angled or any combinations thereof. The elongate member 350 in FIG. 10 is also generally configured to lie in a single plane in both the retracted and extended configurations, but in other embodiments, one or more rigid or flexible sections may be oriented out of plane in the retracted and/or extended configurations. As further illustrated in FIG. 10, the shaft 368 may comprise a groove 369, or a region of the shaft with a narrow diameter or axial transverse dimension, which may reduce the overall cross-sectional area of the tissue removal device 352 by permitting the elongate member 352 to protrude less when in the retracted configuration.

As shown in FIG. 10, the elongate member 350 in the extended state may have flexible sections 366 and 360 located about its proximal and distal openings 370 and 372. In other embodiments, however, the elongate member may have a rigid section or other structure about the proximal or distal openings in the extended state. In FIG. 11, for example, the tissue removal device 380 comprises a generally symmetrical elongate member 382 with proximal and distal rigid members 384 and 386 interconnected by a flexible cable 388. In the extended configuration, the rigid members 384 and 386 are partially located or recessed within the proximal and distal openings 390 and 392 of the rotatable shaft 394. In some further embodiments, having rigid members 384 and 386 at the proximal and distal openings 390 and 392 may reduce the tilting or bending of the elongate member 382 with respect to the shaft 394. The degree with which the elongate member 382 is restricted may depend, for example, on the widths of the openings 390 and 392 and the rigid member 384 and 386, the lengths 396 and 398 of the rigid member 384 and 386 outside and inside the shaft 394, the lengths 400 of the flexible segment(s), and the overall diameter of the shaft 394, and the degree of rigidity of the rigid members 384 and 386. As further shown in FIG. 11, the shaft 394 may further comprise a groove 400 or other configuration with a reduced diameter or transverse axial dimension. At least a portion of the groove 400 or configuration is located between the proximal and distal openings 390 and 392, but the groove 400 or configuration may also be located proximal or distal to the openings 390 and 392, respectively.

Figure 12A:
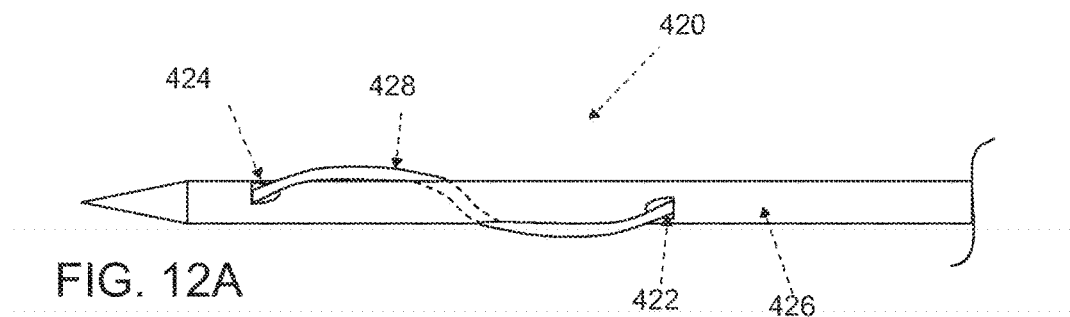
FIGS. 12A and 12B illustrate another embodiment of a tissue removal device with a helically-oriented elongate member in the retracted and extended states, respectively.
Figure 12B:
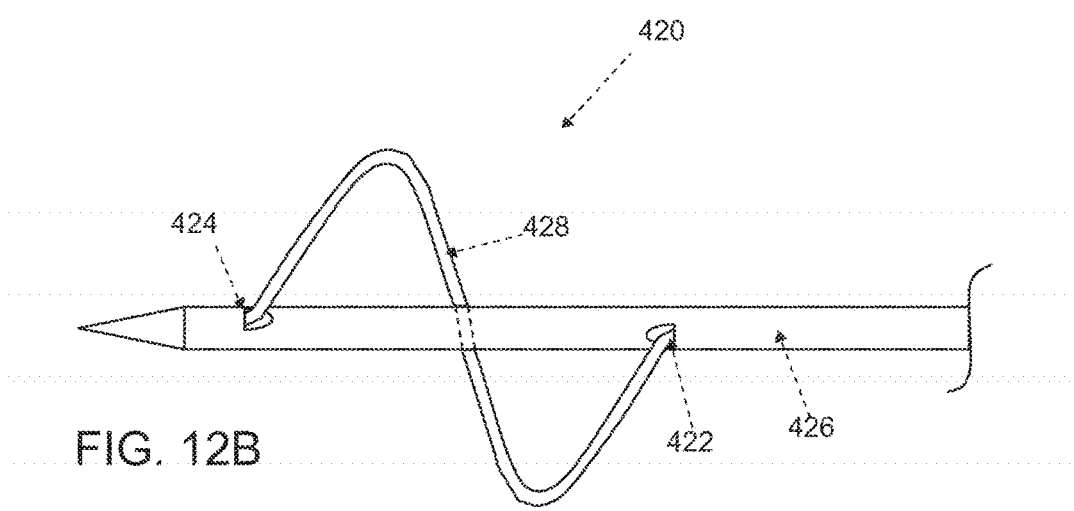

As shown in FIGS. 12A and 12B, in some embodiments, the tissue removal device 420 may have proximal and distal openings 422 and 424 which are located at different circumferential locations along the longitudinal length of the rotatable shaft 426, and/or where the elongate member 428 comprises at least one section having a helical, twisted or skewed configuration with respect to the rotatable shaft 426. FIG. 12A depicts the tissue removal device 420 in a retracted or collapsed configuration, while FIG. 12B depicts the tissue removal device 400 in an extended or expanded configurations. By extending the elongate member 408 through the proximal opening 422 of the shaft 426, the elongate member 426 may become axially compressed and expand radially outward from the shaft 426.

The configuration of the elongate member may vary in the direction of turning. For example, the elongate member may have a right or left-handed spiral orientation (i.e. a clockwise or counter-clockwise orientation). In FIGS. 12A and 12B, for example, the elongate member 428 has a left-handed or counter-clockwise spiral orientation (as viewed from the proximal end of the tissue removal device 420). The spiral orientation of the elongate member 428 may be in the same as the rotation direction of the shaft 426, or be the opposite of the rotation direction. The spiral configuration of the elongate member 428 may be characterized in any of a variety of ways. For example, the absolute number of turns may be the elongate member may be anywhere in the range from about zero (e.g. a linear elongate member) to about 4 turns or more, sometimes about a ¼ turn to about 1½ turns, and other times about ½ turn to about one turn. In other embodiments, the spiral configuration may be characterized by its rate of turning, which may be calculated as the number of turns per millimeter or centimeter. In some embodiments, the rate of turning may be in the range of about 0.3 turns/cm to about 2 turns/cm or more, sometimes about 0.7 turn/cm to about 1.5 turns/cm, and other times about 0.9 turns/cm to about 1 turn/cm. The elongate member 428 may also be characterized by its pitch angle, which may be in the range of about 0 degrees to about 90 degrees, sometimes about 5 degrees to about 90 degrees, and other times about 45 degrees to about 85 degrees. The spiral configuration of the elongate member may be generally curved along its length, but may also comprise multiple linear segments with angled or curved bends in between. The configuration of the spiral elongate member in the retracted and extended configuration may vary, depending upon the flexibility of the elongate member, the manner and angle with which one or more ends of the elongate member are attached or fixed to the rotatable shaft, and the native configuration of the elongate member.

As shown in FIGS. 13A to 13C, a tissue removal device 450 with a spiral elongate member 452 may also comprise one or more grooves 454 on the rotatable shaft 456. The groove 454 may facilitate seating and/or securing of the elongate member 452 in its retracted configuration. As can be seen in FIG. 13C, the spiral configuration of the elongate member 452 and the groove 454 may not be uniform along the length of the rotatable shaft 456. The distal groove 458 adjacent to the distal opening 460 comprises approximately a ½ turn along a longitudinal distance that is about 50% shorter than the ½ turn of the middle groove 462, while the proximal groove 464 between the middle groove 462 and the proximal opening 466 is generally linear. In some embodiments, the change in turn rate may be in the range of about zero to about 4 turns/cm or more, other times about zero to about 1 turn/cm, and other times about zero to about 0.5 turns/cm. In the particular embodiment depicted in FIGS. 13A to 13C, the distal portion 468 of the elongate member 452 remains generally wrapped around the shaft 456 in the distal groove 458 in the extended configuration, while the proximal portion 470 of the elongate member 452 bows radially outward. As can be seen in FIG. 13C, in this particular configuration, the peak displacement distance 472 of the elongate member 452 is located closer to the proximal opening 466 of the shaft 456 than the distal opening 460. The proximal and distal openings 466 and 460 may be oriented perpendicular to the outer surface of the shaft 456, or may be oriented at an angle or tangent with respect to the outer surface of the shaft 456, which may reduce stresses exerted onto the elongate member 452 at the openings 460 and 466. The edges of the groove 454 may also rounded along its length or at least about the openings 460 and 466. The elongate member, however, may be configured with a peak displacement distance located anywhere between the proximal and distal openings, or even extending distal to the distal opening and/or proximal to the proximal opening. In other embodiments, the elongate member may even comprise multiple peak displacement distances (e.g. a multi-angle, undulating or sinusoidal elongate member in the extended configuration). In some embodiments, the peak displacement distance 472 is in the range of about 0.5 to about 10 times greater than the diameter or transverse axial dimension of the shaft 456, sometimes about 1 to about 5 times greater, and other times about 2 times to about 3 times greater. The longitudinal location of the peak distance may be characterized as a relative position from the proximal to distal openings, which may be about −20% or less, about −10%, about 0%, +10%, about +20%, about +30%, about +40%, about +50%, about +60%, about +70%, about +80%, about +90%, about +100%, about +110% or about +120% or more.

Figure 14A:
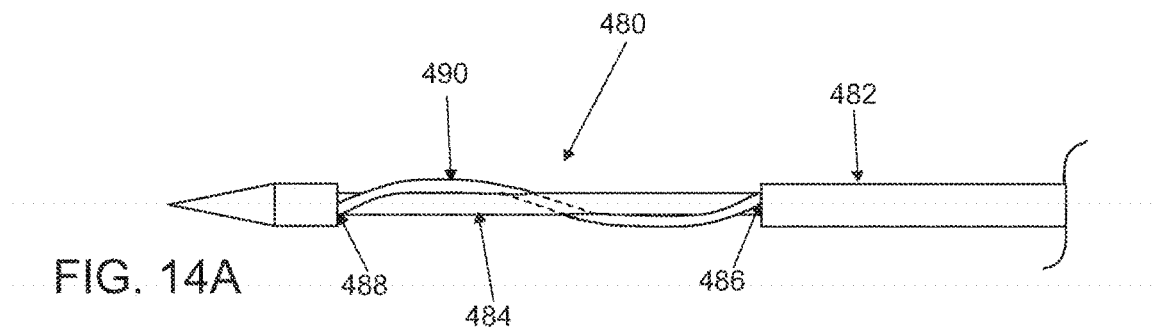
FIGS. 14A and 14B are side elevational views of another embodiment of tissue removal device in the retracted and extended configurations, respectively.
Figure 14B:
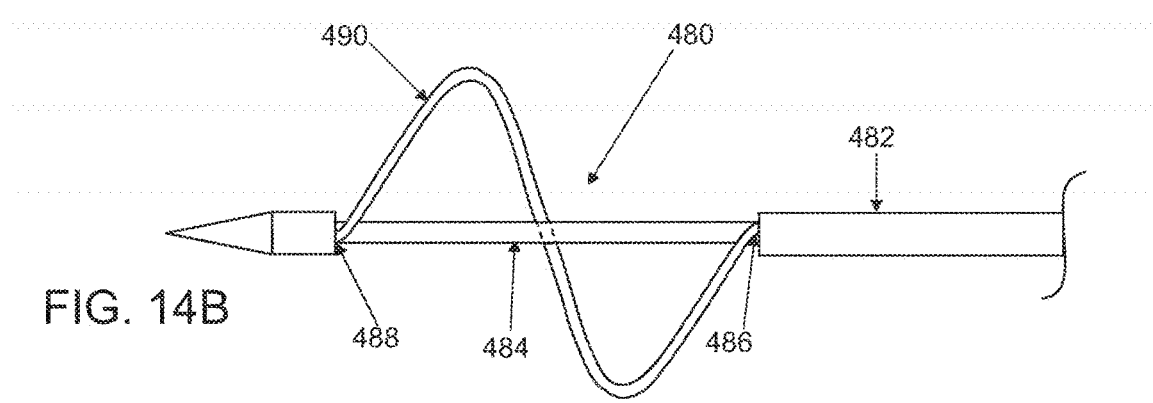

Referring now to FIGS. 14A and 14B, in some embodiments, the tissue removal device 480 may comprise a shaft 482 with a narrowed region 484. At least a portion of the narrowed portion 484 may be located between the proximal and distal attachments or openings 486 and 488 from which the elongate member 490 protrude, but in other embodiments, at least a portion of the narrowed portion 484 may be proximal or distal to the openings 486 and 488, respectively. As depicted in FIG. 14A, the narrowed portion 484 of the shaft 482 may facilitate a low profile retracted configuration, but may also provide additional space for snagged tissue or adhered biological material to occupy. This may occur, for example, when the elongate member 490 in FIG. 14B is retracted into its retracted configuration in FIG. 14A, or during a prolonged procedure. This additional space may be beneficial when withdrawing tissue removal device from an endoscopy instrument or cannula. As further illustrated in FIGS. 14A and 14B, the attachments or openings 486 and 488 may have a transverse axial orientation, rather than the surface orientation of the openings 422 and 424 of the tissue removal device 420 depicted in FIGS. 12A and 12B.

Figure 15:
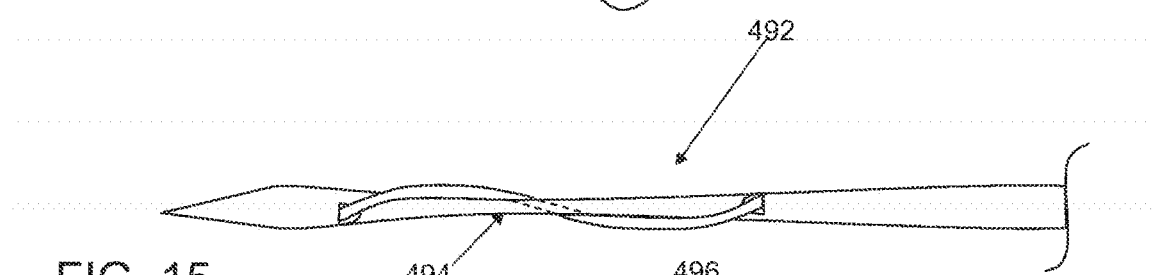
FIG. 15 is an embodiment of a tissue removal device with tapered central region.
Figure 16:
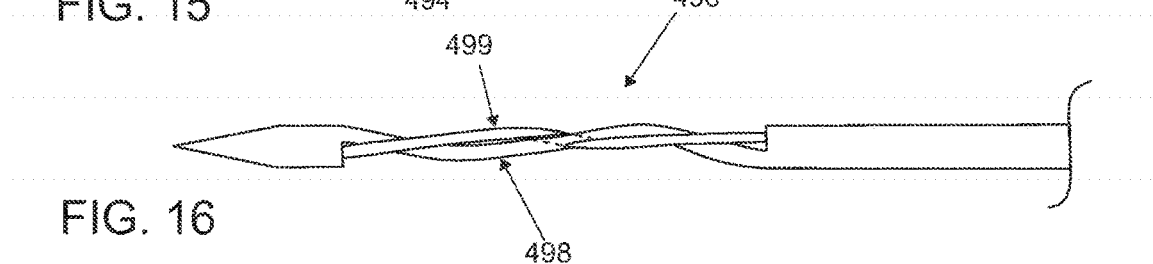
FIG. 16 is an embodiment of a tissue removal device with a narrow corkscrew region.

Although the narrowed portion 484 in FIGS. 14A and 14B has a uniform diameter and configuration, in other embodiments, such as the tissue removal device 492 in FIG. 15, the narrowed portion 494 may have a tapered configuration with a variable diameter or configuration. Referring back to FIGS. 14A and 14B, the longitudinal axis of the narrowed portion 494 may be co-axial with the axis of the rest of the shaft 482, but in some embodiments, the longitudinal axis may be different, e.g. eccentric or variable. In FIG. 16, for example, the tissue removal device 496 comprises a narrowed portion 498 with a non-linear longitudinal axis comprising a helical or corkscrew configuration. Also, although this example of the tissue removal device 496 has narrowed portion 498 and an elongate member 399 with the same helical orientation, in other example, the helical orientations may be different or opposite.

Referring now to FIG. 5B, the tissue removal device 2 in FIG. 5A is illustrated with a portion of the housing 6 removed to show various internal components. In this embodiment, the tissue removal device 2 further comprises a battery 12 to provide power to the motor 14 which drives the tissue removal assembly 8. In other embodiments, a connector to an external power source may be provided in addition to, or in lieu of, the battery 12. The type of battery and power provided may differ depending upon the particular power needs of the motor and/or other components of the tissue removal device 2.

In some embodiments, the motor 14 of the tissue removal device 2 is a DC motor, but in other embodiments, the motor 14 may have any of a variety of configurations, including but not limited to an AC or a universal motor. The motor 14 may be a torque, brushed, brushless or coreless type of motor. In some embodiments, the motor 14 may be configured to provide a rotational speed of about 500 rpm to about 200,000 rpm or more, sometimes about 1,000 rpm to about 40,000 rpm, and at other times about 5,000 rpm to about 20,000 rpm. The motor 14 may act on the tissue removal assembly 8 via the outer tube 4, or a by drive member located within the outer tube 4. In some further embodiments, a fluid seal 16 may be used to protect the motor 14 and/or other components of the housing 6 from any fluids or other materials that may be transported through the outer tube 4, or through the housing aperture 18. In some embodiments, a connector or seal may be provided about the housing aperture 18 to permit coupling of the housing 6 to a trocar, an introducer, a cannula or other tubular member into which the tissue removal assembly 8 and the outer tube 4 are inserted. In some embodiments, the tissue removal device may be used with an introducer or cannula having an outer diameter of about 0.01 cm to about 1.5 cm or more, sometimes about 0.1 cm to about 1 cm, and other times about 2 mm to about 6 mm.

As shown in FIGS. 5A and 5B, the tissue removal device 2 may further comprise a conduit 24 which may be used to connect the tissue removal device 2 and an aspiration or suction source. An aspiration or suction source may be used, for example, to transport fluid or material through a lumen or conduit of the outer tube 4 or through a tubular member in which the outer tube 4 is inserted. In one particular embodiment, the conduit 24 comprises a port 20 which communicates with the fluid seal 16 via a length of tubing 22. The fluid seal 16 is configured to permit flow of fluid or material between the outer tube 4 and the tubing 22, while permitting movement of the outer tube 4 or a drive member therein coupled to the motor 14. In other embodiments, the conduit 24 may further comprise additional components, including but not limited to a fluid or material trap, which may be located within or attached to the housing 6, or attached to the port 20 or the tubing 22, or located anywhere else along the pathway from the tissue removal assembly 8 to the suction source. In some embodiments, a separate port may be provided for infusing or injecting substances into target site using the tissue removal device 2. In other embodiments, the conduit 24 may be used for both withdrawal and infusion of materials and/or fluids, or for infusion only. Depending upon the configuration of the tissue removal device, withdrawal and/or infusion may occur at the distal end of the outer tube 4, and/or through one or more openings of the tissue removal assembly 8. In other embodiments, a port may be used to insert a coagulation catheter, an ablation catheter or other energy delivery device to the target site.

In some embodiments, the outer tube comprises an outer tubular member with at least one lumen, and an elongate drive member configured to mechanically couple the motor to the tissue removal assembly. In other embodiments, the outer tube may contain additional members, for example, to adjust or control the configuration of the tissue removal assembly. In some embodiments, the outer tube 4 may comprise one or more lumens containing control wires, which may be used to manipulate the deflections of the distal end of the outer tube. The outer tube and optional drive members may be rigid or flexible. The outer tube may be pre-shaped with a linear or a non-linear configuration. In some embodiments, the outer tube and the components is configured to be user-deformable, which may facilitate access to particular target sites, or may be user-steerable using a steering mechanism comprising one or more pull wires or tension elements. In some embodiments, a stiffening wire or element may be inserted into the outer tube to provide additional stiffness to the tissue removal device. The length of the outer tube between the tissue removal element and the motor or housing may vary from about 0 cm to about 30 cm or more in some embodiments, sometimes about 4 cm to about 20 cm, and other times about 10 cm to about 14 cm.

In other embodiments, the tissue removal device may comprise a tissue removal assembly that may be detachably attachable to the shaft of a motor or coupled to a motor. In still other embodiments, the tissue removal device may comprise a tissue removal assembly coupled to a shaft, wherein the shaft may be detachably attachable to a motor or a shaft coupled to a motor.

In some embodiments, the housing 6 is configured with a size and/or shape that permits handheld use of the tissue removal device 2. In other embodiments, the tissue removal device 2 may comprise a grip or structure located about the outer tube 4 to facilitate handling by the user, while the proximal end of the outer tube 4 is attached to a benchtop or cart-based machine, for example, or a mounted or fixed machine. In these embodiments, the grip may or may not contain any other components of the tissue removal device, such as a motor, while the machinery at the proximal end of the outer tube 4 may contain one or more other components, such as a suction system or various radiofrequency ablation components, for example. In some embodiments, the housing 6 may have a length of about 1 cm to about 12 cm or more, sometimes about 2 cm to about 8 cm, and other times about 3 cm to about 5 cm. The average diameter of the housing (or other transverse dimension to the longitudinal axis of the housing) may be about 1 cm to about 6 cm or more, sometimes about 2 cm to about 3 cm, and other times about 1.5 cm to about 2.5 cm. The housing 6 may further comprise one or more ridges, recesses or sections of textured or frictional surfaces, including but not limited to styrenic block copolymers or other polymer surfaces.

Figure 17:
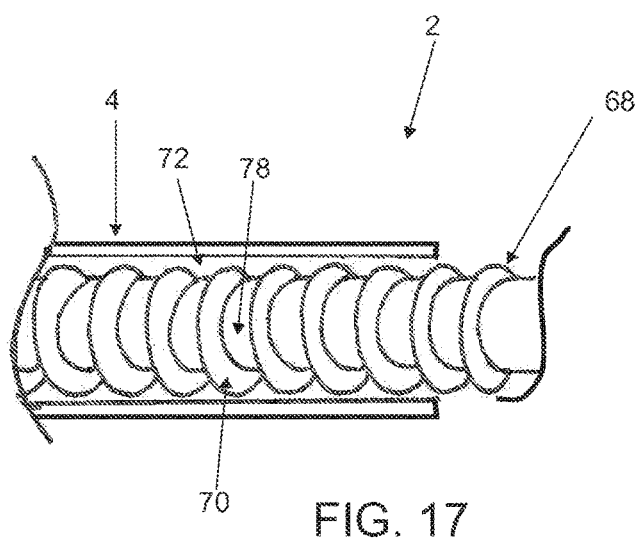
FIG. 17 is a detailed view of one embodiment of an optional tissue transport mechanism.

As illustrated in FIG. 17, a tissue removal device may optionally comprise a tissue transport assembly 68, which may be used to facilitate transport or removal of tissue within or along the outer tube 4. In the particular embodiment depicted, the tissue transport assembly 68 comprises a helical member 70 mounted on a drive member 78 that may be rotated. Actuation of the drive member 78 may mechanically facilitate proximal movement of tissue or other materials within the channel or the lumen 72 of the outer tube 4 by rotating the helical member 70. The actuated drive member 78 will also rotate the distal burr element or other tissue removal assembly 8. In some embodiments, use of the tissue transport assembly 68 may be performed at lower rotational speeds when tissue debulking is not concomitantly performed. When rotated in the opposite direction, the helical member 70 may be used to expel or distally transport tissue, fluid or other materials or agents from the outer tube 4 or supplied to an infusion port of the housing 6.

In some embodiments, the helical member 70 may have a longitudinal dimension of about 2 mm to about 10 cm or more, sometimes about 3 mm to about 6 cm, and other times about 4 mm to about 1 cm. In other embodiments, the longitudinal dimension of the helical member 70 may be characterized as a percentage of the longitudinal dimension of the outer tube 4, and may range from about 5% to about 100% of the longitudinal dimension of outer tube 4, sometimes about 10% to about 50%, and other times about 15% to about 25%, and still other times is about 5% to about 15%. Although the helical member 70 depicted in FIG. 17 rotates at the same rate as the tissue removal assembly, due to their mounting or coupling onto common structure, drive member 78, in other embodiments, the helical member may also be configured to rotate separately from drive member. For example, a helical member may comprise a helical coil located along at least a proximal portion of the lumen of the outer tube but is not mounted on the drive member. In this particular example, the helical member may rotate independently of the drive member. In still other embodiments, the helical member 70 may be mounted on the surface of the lumen 72 and can be used to transport tissue or substances along the lumen 72 by rotation of the outer tube 4, independent of the drive member 78 or a tissue removal assembly.

Although the helical member 70 is depicted as a continuous structure, in some embodiments, the helical member 70 may be interrupted at one or more locations. Also, the degree or angle of tightness of the helical member 70 may vary, from about 0.5 turns/mm to about 2 turns/mm, sometimes about 0.75 turns/mm to about 1.5 turns/mm, and other times about 1 turn/mm to about 1.3 turns/mm. The cross-sectional shape of the helical member 70 may be generally rounded as depicted in FIG. 17, but in other embodiments, may have one or more edges. The general cross-sectional shape of the helical member 70 may be circular, elliptical, triangular, trapezoidal, squared, rectangular or any other shape. The turn tightness and cross-sectional shape or area of the helical member 70 may be uniform or may vary along its length. In some embodiments, multiple the helical members 70 may be provided in parallel or serially within the outer tube 4.

In some embodiments, the drive member 78 may be configured to extend distally and retract from the outer tube 4 by a length of about 0.01 cm to about 2 cm or more, sometimes about 0.02 cm to about 1.5 cm and other times about 0.05 to about 1 cm. In some embodiments, the helical member 70 is located proximal to the tissue removal assembly at a distance of about 0.01 cm to about 2 cm or more, sometimes about 0.02 cm to about 1.5 cm and other times about 0.05 to about 1 cm. In some embodiments, when drive member 78 is maximally extended from outer tube 4, helical member 70 may protrude from outer tube 4 by a longitudinal dimension of about 0.01 cm to about 2 cm or more, sometimes about 0.1 cm to about 1 cm, and other times about 0.25 cm to about 0.5 cm. In some embodiments, the degree of extension of the drive member 78 and/or the helical member 70 may affect the degree of tissue transport by the tissue transport assembly.

Figure 18A:
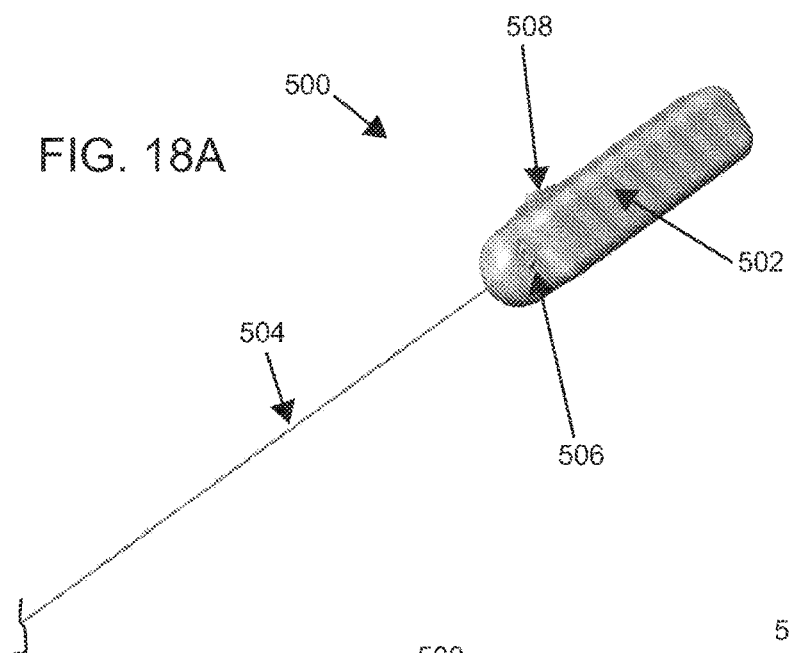
FIGS. 18A and 18B are perspective and side elevational views of another embodiment of a tissue removal device.
Figure 18B:
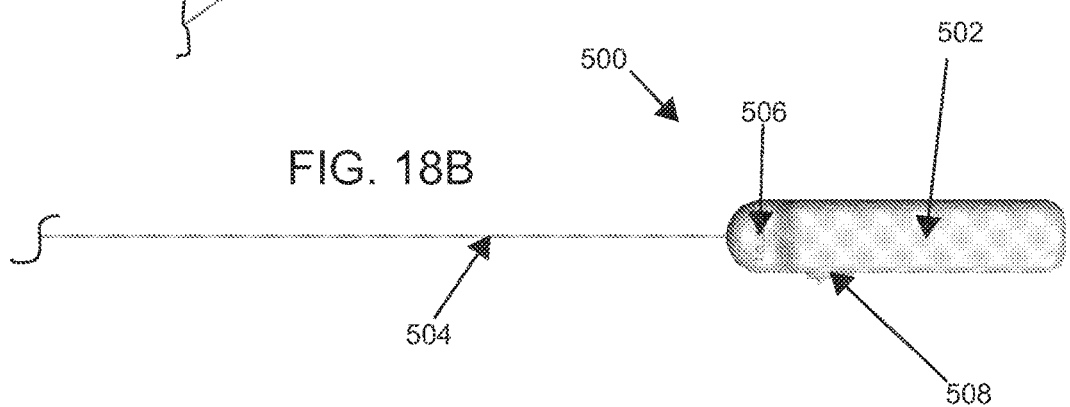

Referring to FIGS. 18A and 18B, in another embodiment, a tissue removal device 500 comprises a housing 502 and an outer shaft 504. The housing 502 may include an adjustment mechanism with a thumbwheel 506 configured to adjust the retraction and extension of extendable tissue removal assembly (not shown). The thumbwheel 506 may provide a continuous range of change to extendable tissue removal assembly, but in other embodiments, the turning of thumbwheel 506 may be configured with clicks or detents that provide one or more preset positions. As mentioned previously, any of a variety of other control mechanisms and interfaces may be used. The adjustment mechanism may comprise one or more blocking elements or other adjustment limiting configurations to resist or prevent overextension of extendable tissue removal assembly. For example, limit structures may be provided in housing 502 to resist overextension of extendable tissue removal assembly (not shown). In this particular embodiment, tissue removal device 500 is configured to rotate the tissue removal assembly at a fixed rotational speed, controllable by a rocker-type power switch 508. As mentioned previously, however, any of a variety of power and/or speed control mechanisms may be used.

Figure 18C:
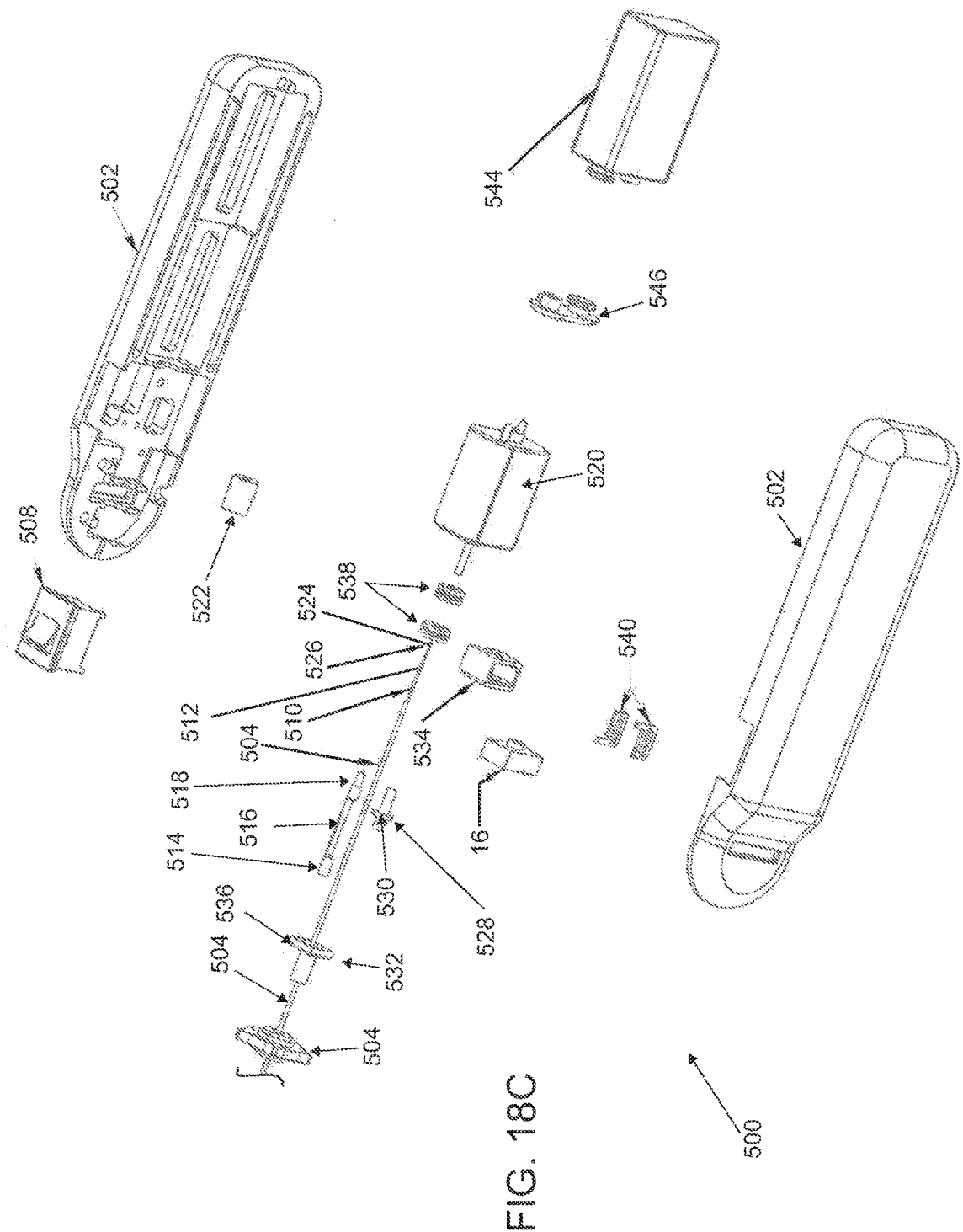
FIG. 18C is a component view of the tissue removal device in FIGS. 18A and 18B.
Figure 18D:
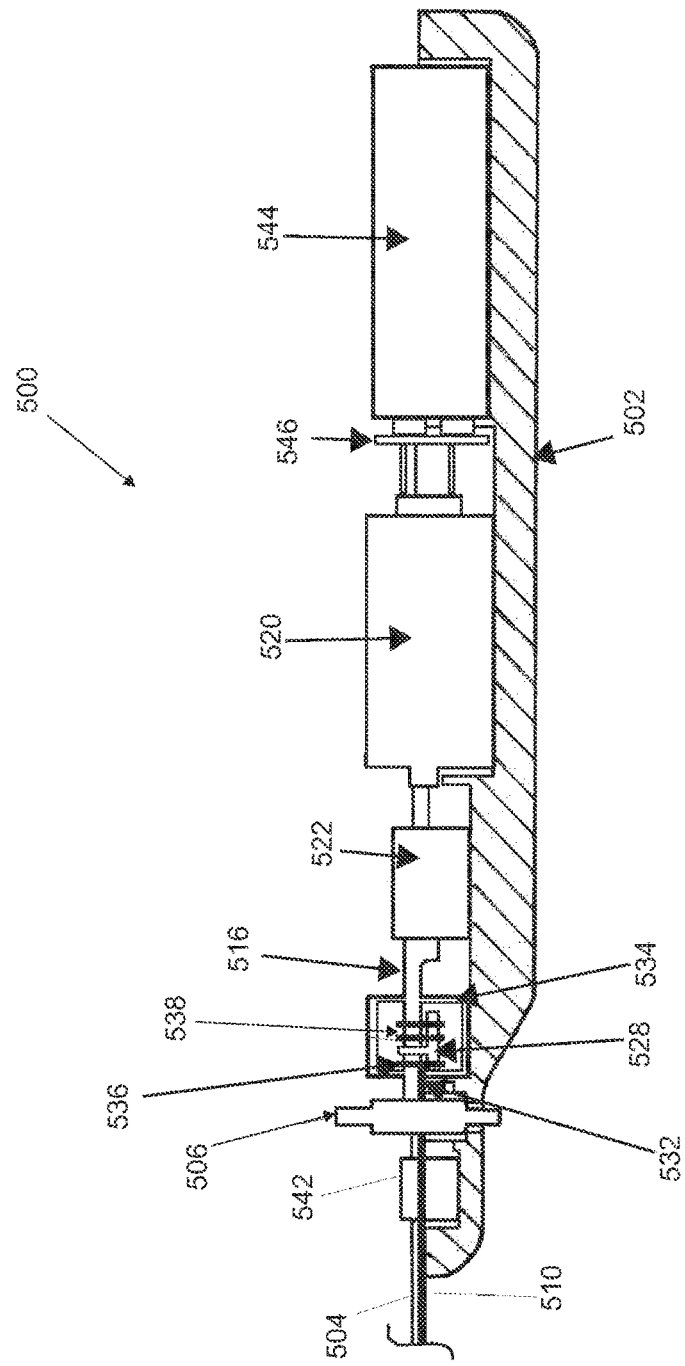
FIG. 18D is a cross-sectional view of the tissue removal device in 18A and 18B with a portion of the housing removed.

Referring to FIGS. 18C and 18D, FIG. 18C is a component view of the internal components within housing 502, while FIG. 18D is a schematic cross-sectional view of the internal components with a portion of housing 502 removed. As shown in FIG. 18C, a drive member 510 rotatably resides within the outer shaft 504 of the tissue removal device 500. The distal end (not shown) of the drive member 510 is coupled to the tissue removal assembly (not shown), while the proximal end 512 of the drive member 510 is coupled to the distal end 514 of a driveshaft 516. The proximal end 518 of the driveshaft 516 may be coupled to a motor 520, either directly or through a coupler 522. The coupler 522 may be configured to permit some axial movement of driveshaft 526. The proximal end 524 of an adjustment member 526 protrudes from the proximal end 510 of drive member 512 and is attached to a drive key 528. The drive key 528 may comprise a flange 530 that is slidably located between the proximal and distal ends 518 and 514 of the driveshaft 516. The thumbwheel 506 may be movably coupled to a thrust member 532 so that the rotation of the thumbwheel 506 results in the axial movement of thrust member 532. In some embodiments, the thrust member 532 may be configured with helical threads that are complementary to a threaded lumen of the thumbwheel 506. In other embodiments, however, the thrust member may comprise a slide member, a pivot member or other coupling structure. The thrust member 532 may be configured to axially slide the drive key 528 through a retaining structure 534 which movably couples the thrust member 532 to the drive key 528. The retaining structure 534 permits the rotation of the driveshaft 516 by the motor 520 while also coupling the axial movements of the thrust member 532 to the drive key 528, thereby permitting adjustment of the tissue removal assembly located at the distal end of the shaft 504 while maintaining the ability of the drive member 510 to rotate. The thrust member 532 may comprise a flange 536 to facilitate retention of the thrust member 532 within the retaining structure 534. The flange 536 may comprise one or more bearings to facilitate rotational movement of the drive key 528 against the non-rotating flange 536. The retaining structure 534 may also contain one or more retaining bearings 538 to facilitate the rotation of the driveshaft 516 against the drive key 528 while transmitting any axial forces to the drive key 528. The retaining structure 534 is optionally provided with one or more limiters 540, which may be used to restrict overextension or retraction of the tissue removal assembly. A seal 542 may be provided around the outer shaft 504 to protect the contents of the housing 502.

As illustrated in FIG. 18D, the tissue removal device 500 may be powered using a battery 544 that is coupled to the motor 520 using a battery connector 546. As depicted in FIG. 18C, battery 544 may be a standardized battery, such as a 9-volt battery, but may also be a customized battery. Other examples of drive shafts couplings and adjustment mechanisms that may be used are disclosed in U.S. Pat. No. 5,030,201, which is hereby incorporated by reference in its entirety.

In the various examples described herein, the outer tube and the driveshaft of the tissue removal device may comprise a rigid structure and material, but may also optionally comprise at least one flexible region which may bend while still permitting rotation of the driveshaft. Examples of flexible driveshafts that may be used are disclosed in U.S. Pat. Nos. 5,669,926 and 6,053,907, which are hereby incorporated by reference in their entirety. In some examples, the flexible region(s) may comprise a substantial portion or all of the length of the driveshaft and outer tube. A tissue removal device with a flexible region may facilitate access to certain regions of the body, such as the central spinal canal through an intervertebral foramen. In some examples, the flexible tissue removal device may comprise a steering assembly that uses one or more steering wires that are attached distal to the flexible region and manipulated by a steering member in the proximal housing. Other steering mechanisms used with catheters and other elongate instruments may also be used. In other examples, an active steering mechanism is not provided on the flexible tissue removal device, but the flexible tissue removal device may be steered by an endoscopic instrument into which the tissue removal device has been inserted. Some examples of steerable endoscopic instruments are disclosed in Application No. 61/045,919, which is hereby incorporated by reference in its entirety.

Figure 19C:
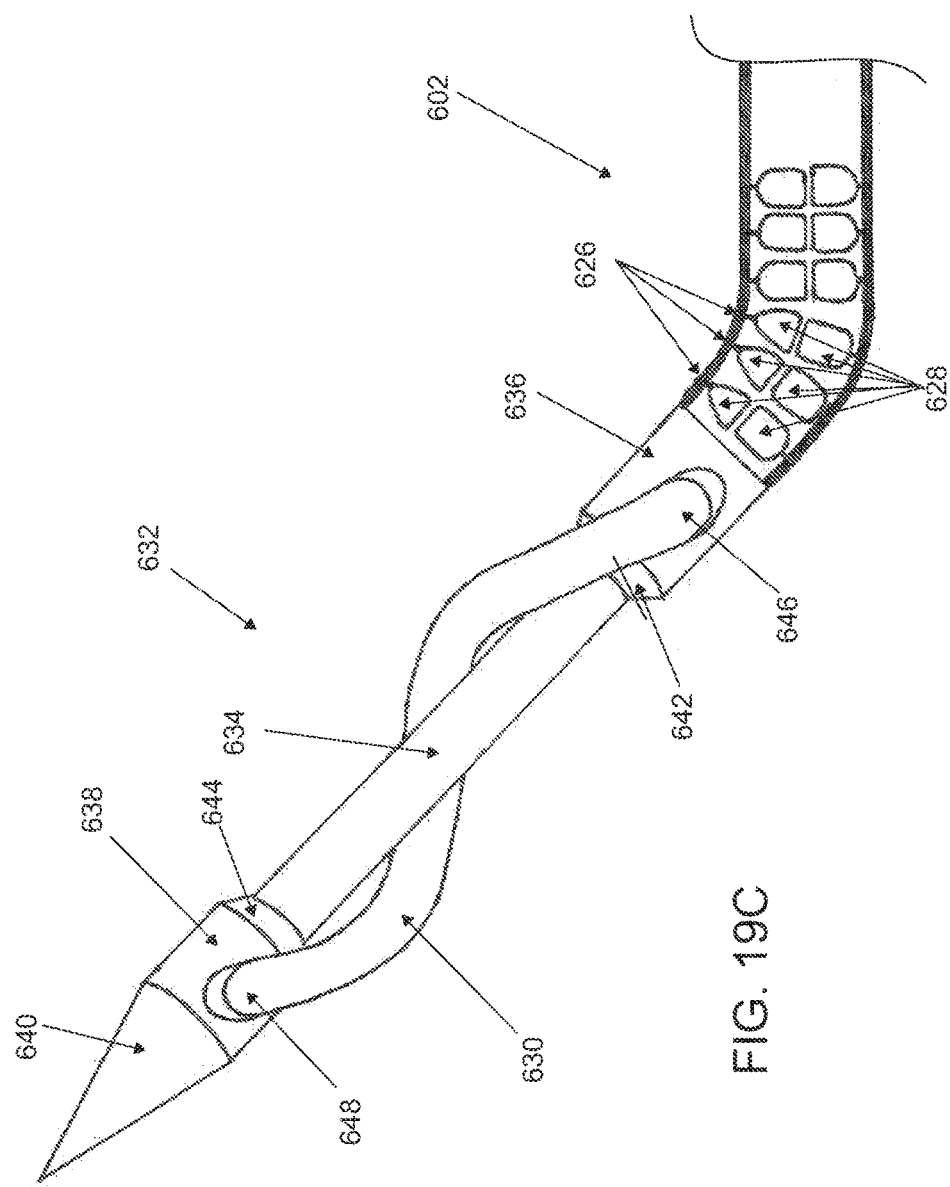
FIG. 19C is a detailed view of the distal end of the flexible tissue removal device of FIG. 19A in a bent configuration.

FIGS. 19A to 19C depict one embodiment of a tissue removal device 600 with a flexible region 602 and a steering assembly 604 located in the housing 606 of the tissue removal device 600. In addition, the housing 606 includes a power switch 608 which actuates the motor 610 that rotates the driveshaft (not shown) located in the outer tube 612, and an irrigation tube 614 which may be used infuse fluid or provide suction about the distal end of the device 600. As shown in FIG. 19B, the steering assembly 604 comprises a pivoting lever 616 with two arms 618 and 620 protruding from the housing 606. In other embodiments, the steering assembly 604 may comprise a single arm lever, a slider, knob or other type of actuator. The steering assembly 604 may optionally comprise one or more springs or bias structures, which may facilitate springback of the lever 616 once released. The steering assembly 604 may also optionally comprise a releasable locking mechanism to maintain the steering assembly in a particular configuration. The locking mechanism may be a frictional interfit or an interlocking mechanism, for example.

Coupled to the lever 616 are two steering elements or wires 622 and 624, which are slidably movable within the outer tube 614 and are distally coupled to a distal site of the flexible region 602. The steering wires 622 and 624 may be separate wires, or two segments of the same wire looped through the lever 616. When a steering wire 622 or 624 is tensioned by actuating one of the lever arms 618 and 620, the flexible region 602 will curve or bend. The flexible region may comprise any of a variety of flexible materials and/or flexible structures, including any of a variety of polymeric or metallic structures. In the depicted embodiment, the flexible region 602 comprise a plurality of optional slots 626, which may augment the bending characteristics, but in other embodiments, an accordion-like configuration or other type of bending configuration may be provided. The ends 628 of the slots 626 depicted in FIG. 19C have optional enlarged arcuate configurations, which may redistribute at least some of the bending forces that may act of the flexible region 602 and may resist tearing or reduce any resulting damage to the flexible region. The length of the flexible region may be in the range of about 1 mm to about 200 mm or more, sometimes about 5 mm to about 50 mm, and other times about 8 mm to about 30 mm. The width of the ends 628 of the slots 626, as measured in the unbent configuration along the longitudinal axis of the tissue removal device, may be in the range of about 0.5 mm to about 4 mm or more, sometimes about 1 mm to about 3 mm, and other times about 1 mm to about 2 mm. In still other embodiments, the flexible region may lack a particular configuration but comprises a flexible material that has a lower durometer than the other portions of the outer tube. The maximum degree of bending may vary from about 5 degrees up to about 10 degrees or more, sometimes about 15 degrees up to 25 degrees or more, and other times about 45 degrees to about 75 degrees or more, and even about 90 degrees to about 105 degrees or more in certain embodiments. In embodiments of the tissue removal device having bi-direction steering from its neutral axis, the maximum degree of bending in each direction may be the same or may be different.

As illustrated in FIG. 19C, a flexible elongate member 630 is coupled to a rotatable shaft assembly 632 comprising a reduced diameter core 634 located between a proximal and distal sections 636 and 638. A piercing element 640 may be attached to the distal end of the rotatable shaft assembly 632. The proximal and distal sections 636 and 638 each comprise optional taper regions 642 and 644. In some embodiments, the taper regions 642 and 644 may reduce or eliminate the potential snagging of the elongate member 630 during retraction, or snagging of the rotatable shaft assembly 632 during its insertion or withdrawal with respect to the vertebral disc, the epidural space, or the cannula or endoscopic device in which it was placed. In the retracted configuration illustrated in FIG. 19C, the elongate member 630 has a helical orientation about the reduced diameter core 634, but may or may not be contacting the core 634.

As depicted in FIG. 19C, the exposed proximal and distal ends 646 and 648 of the flexible elongate member 630 may be coupled to the rotatable shaft assembly 632 through either openings or attachment sites located on the circumferential surfaces of the proximal and distal ends 646 and 648. Other sites where one or both ends of the flexible elongate member 630 may be coupled include but are not limited to the taper regions 642 and 644, if any, or any other transversely surface have at least some degree of transverse orientation with respect to the longitudinal axis of the rotatable shaft assembly 632. Still other coupling sites may include the reduce diameter core 634 and the piercing element 640.

A steerable tissue removal device may be used during some procedures to increase the region or amount of tissue removed, compared to a rigid tissue removal device, for example. In some instances, anatomical restrictions or increased risks of injury may limit the range with which a rigid tissue removal device may be manipulated. FIGS. 20A and 20B, for example, schematically depict some of the movement axes and the potential tissue removal zones that may be achieved with a steerable tissue removal device 650. Here, a steerable tissue removal device 650 with an extendable cable 652 may be inserted into a vertebral disc 653. While the steerable tissue removal device 650 and a rigid linear tissue removal device may translate and rotate with respect to its longitudinal axis 654, the pivoting range 656 of the rigid portion of the outer tube 658 of the tissue removal device 650 (and the corresponding structure on a rigid tissue removal device) may be substantially limited because even small angular movements of the outer tube 658 may be require substantial absolute displacement of the more proximal portions of the outer tube 658. This displacement, however, will be limited by the amount, the location and/or the compliance of the body tissues and structures between the proximal end (not shown) and the distal end 660 of the rigid portion of the outer tube 658. In contrast, a tissue removal device 650 with a flexible segment 662 located distally permits a range of angulation or bending 664 from the longitudinal axis 654 of the tissue removal device 650 without requiring substantial displacement or leveraging of the rigid portion of the outer tube 658. Thus, the flexible segment 662 may be able to reach tissue that is spaced apart from the longitudinal axis 654 with less physical effort, and may be even be able to reach tissue that cannot be reached by pivoting a rigid portion of the outer tube 658.

In addition to the bending of the flexible segment 662, the steerable tissue removal device 650 may also access tissues located away from the longitudinal axis 654 by increasing the extension of the extendable cable 652 along its extension range 665. The extension range 665 may be characterized as a dimension that is perpendicular to the longitudinal orientation of the core section 668 to which the extendable cable 652 is coupled. For example, a tissue removal device with a 1 mm diameter core and configured with an extendable cable that may be adjusted to a perpendicular distance of 3 mm away from the core can remove tissue in a zone that is 7 mm in at its maximum diameter (i.e. 1 mm shaft plus 2 times 3 mm of the rotated elongate member). In embodiments where the extendable cable is extended to a greater degree, even greater volumes or zones of tissue removal may be achieved. Thus, by manipulating the degree of cable extension, the volume or range of tissue removal that may be performed may be adjusted without requiring repositioning the tissue removal device, either by torqueing its shaft or using its steering mechanism (if any).

Because the particular tissue removal device 650 in FIGS. 20A and 20B permits the actuation of the extendable cable 652 while the flexible segment 662 is bent by providing a flexible or bendable driveshaft (not shown), the tissue removal zone 670 may be displaced away from the longitudinal axis 654. Furthermore, because each of the movement described above may be synergistically combined with one or more other movements, even greater larger tissue removal zones may be achieved. For example, rotation 672 of the bent tissue removal device 650 around the longitudinal axis 654 by torqueing the rigid portion of the outer tube 658, may achieve an even larger tissue removal zone 674. The rotation 672 of the bent tissue removal device 650 may occur while the extendable cable 652 is being rotated, or when the cable 652 is not rotating. The amount of rotation 672 may be anywhere in the range of about 1 degree to about 360 degrees or more. Any of a variety of combinations of cable extension, flexible zone bending, and outer tube rotation and translation may be used to achieve the desired tissue removal.

While various flexible, steerable and rigid embodiments of the tissue removal device may be used to remove larger volumes of tissue as described above, in other embodiments, a tissue removal device may be used to perform focal debulking of tissue. For example, by utilizing the small profile and/or the steerable features of certain embodiments of the tissue removal device, the tissue removal device may be more accurately positioned or navigated to a specific target site in a body structure. In some instances, the removal of lower volumes of tissue at a specific target location may be used to achieve a desired result, in comparison to the removal of a larger volume of tissue from a general target location. Furthermore, by adjusting the cable or tissue removal element relative the shaft of the tissue removal device, the volume of mechanical tissue removal may be adjusted relative to the shaft without requiring repositioning of the shaft. By removing less disc tissue to reduce a herniation, for example, a larger amount of non-pathologic disc tissue and structural integrity of the disc may be preserved. In some instance, relatively greater preservation of the disc tissue which may slow the rate of further disc degeneration and reherniation compared to lesser degrees of tissue preservation.

In one example, a herniated disc may be accessed and visualized endoscopically. A steerable tissue removal device may be inserted into the disc and steered toward the region of herniation, rather than to the center of the disc, for example. The extendable cable or other adjustable tissue removal element is actuated to pulverize an initial amount of tissue at the region of herniation and removed by the auger. In some embodiments, to facilitate controlled volume tissue pulverization, the distance between the couplings of the extendable cable to its rotatable shaft may be less than about 10 mm, sometimes less than about 7 mm, and other times less than about 5 mm. To facilitate precise removal of the pulverized tissue, the distal suction opening of the tissue removal device may be located less than about 10 mm from the proximal coupling of the extendable cable, sometimes less than about 7 mm, and other times less than about 5 mm or about 3 mm. After the initial actuation of the extendable cable, the herniation is reevaluated endoscopically and the degree of cable extension may be adjusted higher in a stepwise manner and reevaluated until the desired reduction in the herniation is achieved.

In some uses of the tissue removal device, in both steerable and non-steerable configurations, the tissue removal zones may positioned whereby structures such as the annulus fibrosus and the vertebral body endplates may be unintentionally damaged or contacted. In embodiments where the tissue removal device has been configured as described previously to limit or avoid significant damage to these structures, greater tissue removal may be safely achieved even when the distal tip of the tissue removal device cannot be directly visualized, e.g. when the endoscope is located in the epidural space while the tissue removal device is located inside the vertebral disc.

In some instances, embodiments of the tissue removal device may be characterized by the ratio of the maximum diameter or cross-sectional area of tissue removal of a rotating extended elongate member, and the diameter or cross-sectional area of the outer tube of the tissue removal device or the tissue pathway formed by the tissue removal device. In the example described above, the diameter of the elongate member in its rotating deployed configuration to the diameter of the outer tube is a ratio of about 7:1. In some embodiments, this ratio is at least about 3:1 or higher, but in other embodiments, the ratio is at least about 5:1 or higher, or even about 10:1 or about 20:1 or higher in certain embodiments. In other examples, the tissue removal device may be characterized by the maximum perpendicular distance that the elongate member may be extended, or by the ratio of this distance to the diameter (or an axial transverse dimension) of the outer tube. In some examples, this ratio is at least about 3:1 or more, sometimes about 5:1 or more, or even about 7:1 or about 10:1 or more.

Examples of procedures that may be used to access the spine are disclosed in U.S. Pat. No. 7,108,705, U.S. Pat. No. 4,573,448, U.S. Pat. No. 6,217,5009, and U.S. Pat. No. 7,273,468, which are hereby incorporated by reference in their entirety. The various embodiments of the tissue removal device disclosed herein may be used to perform a discectomy or nucleotomy, but may also be used to perform any of a variety of tissue removal procedures in the spine and outside of the spine. The tissue removal device may be used in minimally invasive procedures as well as open surgical procedures or limited access procedures. These procedures may include but are not limited to interlaminar, translaminar and intralaminar access procedures. In one particular embodiment, a patient may be placed into a prone position with a pillow or other structure below the abdomen to limit lumbar lordosis. The patient is prepped and draped in the usual sterile fashion and anesthesia is achieved using general, regional or local anesthesia. Under fluoroscopic guidance, a sharp tipped guidewire, or a needle with a guidewire may be inserted into the paravertebral space or epidural space from a posterior or postero-lateral location of the patient's back at a location in the range of about 5 cm to about 15 cm lateral to the midline. In some instances, guidewire insertion may be facilitated by inserting a needle into the tissue first. In alternate embodiments, an anterior procedure through the abdominal cavity or anterior neck region may be performed. Once access to the target location is confirmed, a dilator may be used with the guidewire to enlarge the insertion pathway. Then, an introducer or cannula may be inserted over the guidewire, followed by subsequent guidewire removal and insertion of an endoscope into the introducer or cannula. Alternatively, an endoscope may be inserted over the guidewire. The endoscope may be manipulated or steered to directly visualize and identify the relevant structures such as the disc, the nerve or other adjacent structures and site(s) of tissue removal. In some embodiments where the patient is under local or regional anesthesia, the suspected nerve impingement may be confirmed by contacting or manipulating the suspected nerve with the endoscope, or other device inserted through the endoscope, and assessing the patient's response or symptoms. One embodiment of an endoscope that may be used is described in U.S. Application No. 61/045,919, which has been hereby incorporated by reference in its entirety. Once the target region has been evaluated, a tissue removal device may be inserted through the spinal access device or endoscope and to pierce through the annular wall of a herniated disc. Once inserted, the tissue removal device is manipulated the elongate member to its extended or deployed configuration and actuated to emulsify or pulverize the tissue of the nucleus fibrosus. In some embodiments, the tissue removal device may be actuated for a duration in the range of about 5 seconds to about 90 seconds or more, sometimes about 15 seconds to about 60 seconds, and other times about 30 seconds to about 60 seconds. The pulverized material may then be suctioned through the device and then the effect of the tissue removal may be re-evaluated by the endoscope or other visualization mechanisms. In some embodiments, a liquid or lubricant may be injected or infused into the treatment site. In some examples, the liquid or lubricant may be useful to facilitate removal of the pulverized material, including but not limited to vertebral discs that may be desiccated. In other examples, the liquid or lubricant may be injected or infused before or during the actuation of the tissue removal device. In some examples, the liquid or lubricant may comprise a contrast agent that may facilitate viewing of the tissue site on fluoroscopy, x-ray, CT, MRI, ultrasound or other imaging modalities. The contrast agent may be used at any time or at multiple times during the procedure, including but not limited to confirmation of guidewire or tissue removal device placement, and also to verify the volume and/or location of tissue removal. In some specific embodiments, actuation of the tissue removal device may be stopped to verify that annulus of the vertebral disc or the cortical bone of the vertebral body has not been compromised. Also, in some examples, the contrast agent may be injected and imaged after device to assess proper operation of the device, including but not limited to tissue pulverization and aspiration mechanisms.

During actuation, the tissue removal device may be held in place or may be moved around the treatment site. The movement may include moving the device back and forth along its insertion access, side to side, up and down, or with an orbital motion (clockwise or counterclockwise), or any combination thereof. The range of cable displacement from the rotatable shaft may also be cyclically varied during device actuation. The cycling movements may be performed based upon tactile feedback or rotational resistance of the device, or may be done in repeating motion with an average frequency in the range of about one complete motion about every 0.5 sec to about 4 seconds, about 1 second to about 2 seconds, or about 0.5 seconds to about 1.5 seconds, for example. The duration of each cycling period may be in the range of about 1 second to about 30 seconds or more, about 3 seconds to about 20 seconds, about 5 seconds to about 10 seconds, for example. Suction or aspiration may be applied during these motions to assess the amount of tissue pulverized and removed.

The actuation of the tissue removal device may be repeated as desired to remove disc material. In some embodiments, the tissue removal device may be withdrawn from the disc and reinserted directly into or against the extruded disc material and actuated. Once the tissue removal is completed, the tissue removal device may be withdrawn. The puncture site in the annular wall may have a cross-sectional area of less than about 2 mm$^2$ or less, sometimes about 1 mm$^2$ or less, and other times about 0.9 mm$^2$ or less, and thus may self-seal without requiring treatment of the puncture location with an adhesive, a suture or coagulation probe. The body location may be rechecked with the endoscope or spinal access device to verify that no bleeding or comprise of the integrity of the disc or spinal nerves has occurred, and then the endoscope or spinal access device is removed from the body and the skin access site is bandaged.

While the embodiments described above may be used to remove soft tissue without substantially removing calcified or bony tissue, in other embodiments, the tissue removal device may be configured to remove bone. In some examples, this may include configuring the tissue removal device various bone-removing coatings and/or a higher rotational speed. The coatings may comprise coarser grit structures made from materials including, but not limited to titanium nitride, chrome alloy coating, tungsten carbide, diamond grits, silicon carbide grits, ceramics, or other suitable materials. The spiral cable may be spun at high speed (e.g. about 10,000 rpm to about 30,000 rpm or more) to grind the bone to smaller pieces that can be aspirated by the auger. Saline irrigation may be used to clean and/or cool the spiral cable and/or the surround tissue. In some further configurations, the tissue removal device may be further configured to differentially removing cancellous bone while generally preserving compact bone. Such a tissue removal device may be used, for example, to form a passageway or cavity within a vertebral body or a long bone without disrupting the integrity of the outer surface of the bony structure.

In one example, a hollow needle or trocar may be passed through the spinal muscles until its tip is precisely positioned within the fractured vertebra. This may be performed under external imaging guidance (e.g. fluoroscopy, CT or ultrasound) or using an endoscopy system. In other examples, intraosseous venography may be performed in conjunction with other visualization modalities. In some instances, intraosseous venography may be used to visualize the basivertebral venous plexus or a paravertebral vein and to possibly avoid inadvertent entry into these structures.

Upon reaching the outer surface of the vertebral body, the distal tip of the tissue removal device (e.g. the distal head 336 of the tissue removal device 300 in FIG. 8) may be used to penetrate the compact bone of the vertebral body to provide access to its interior. In other embodiments, a bone penetration device, such as a trephine or a burr, may be used to form a channel or passageway into the vertebral body. The bone penetration device is then removed and the cable-based tissue removal device may be inserted into the passageway and into the vertebral body. In other embodiments, the tissue removal device may be provided with a distal burr or drill head rather than a conical head. In some examples, the spiral cable is displaced radially outward before the rotating is initiated, while in other examples, rotation is initiated first before the spiral cable it let out. In some examples of vertebroplasty, the spiral cable may have a maximum radial displacement of about 4 mm, about 5 mm, about 6 mm, about 7 mm, or about 10 mm or more. In some examples, the volume of space formed by the tissue removal device may be further augmented similar to the range of tissue removal disclosed for removal of annular tissue depicted in FIGS. 20A and 20B. As mentioned previously, the spiral cable may be rotated in the directional sense as the spiral configuration, but may also be rotated in the opposite direction.

The spiral cable may be as a single filament or a multi-filament cable. Each filament may comprise the same or a different material or configuration. In some examples, each filament comprises stainless steel (e.g. 304, 316 or 17-4 stainless steel) which is wound into a cable. The stiffness of the cable may be altered by the changing the tightness of the winding, the number of filaments, and/or the thickness of the filaments. One or more of these characteristics, in combination with an optional grit surface may be used to adjust the preferential grinding features of the tissue removal device. In some procedures, by preferentially cutting the cancellous bone while preserving the compact bone, the compact bone shell or structure of the vertebrae or other bone may protect the soft tissue structures located outside the shell or surface. The compact bone shell or structure may also restrict flow of any bone cement injected into the target site. In some examples, contrast dye or other visualization agents may be injected into the target site to assess the integrity of the target site prior to cement injection or other treatments.

In another example, depicted in FIGS. 21A to 21D and FIG. 22, the tissue removal system 700 may comprise an extendable spiral cable 702 with a blunt distal tip 704. In some instances, a blunt distal tip 704 may be used when a passageway or channel has been previously formed, or when blunt dissection is sufficient. For example, during a discectomy or a vertebroplasty procedure, a cannula 706 containing a removable obturator with sharp distal end 708, as shown in FIG. 23, may be used to form a passageway or channel through the tissue surrounding the spine and/or through the surface of a vertebra. The obturator may be removed from the cannula 706 to insert the tissue removal system 700. In other examples, a trocar with a sharp distal end may be used to form a passageway and then removed to permit insertion of the tissue removal system 700. Alternatively, a trephine or bone burr, which may be either motorized or manually activated, may be used with the cannula 706, in addition to or in lieu of the obturator. The cannula 706 may comprise an optional proximal connector 709, such as Luer lock, to releasably couple the obturator and/or the tissue removal system 700.

Referring to FIG. 21A, which depicts the spiral cable 702 in an extended position, and to FIGS. 21B to 21D, which depicts the spiral cable 702 in a retracted position, the cable 702 is attached distally to the blunt distal tip 704 and proximally to a base 710. The cable 702 may be partially recessed in channels 712 and 714 of the tip 704 and base 710. Between the tip 704 and base 710 is a cable shaft 716 with a cross-sectional size that is smaller than the tip 704 and/or base 710. In other embodiments, the cable shaft may have a cross-sectional size that is similar to or greater then the tip 704 or base 710. The cable shaft may also comprise an optional groove or recess to at least partially retain the cable 704 when in a retracted position.

FIGS. 21A to 21D further depict an optional feature of the tissue removal system 700 comprising an outer tubular shaft 718 with a cutting edge 720. In this particular example, the cutting edge 720 is a beveled edge, which may or may not be at least partially sharpened. In other examples, the cutting edge may be sharpened but not beveled. As further depicted in FIGS. 21A to 21D, the inner shaft 722 located in the outer tubular shaft 718 may comprise at least one optional thread structure 724 which is configured to draw fluids and/or other materials into the outer tubular shaft 718 for removal from the target site. A beveled or sharpened edge may further shear or break-up materials pulled into the outer tubular shaft 718 by the thread structure 724. In some examples, the rotational sense of the thread structure 724 may be the same as the spiral cable 702, but in other examples, the thread structure 724 and the spiral cable 702 may be opposite rotational senses.

The thread structure 724 may be made from the same or a different material as the inner shaft 722 and/or the outer tubular shaft 718. In some examples, use of a different material between the thread structure 724 and the outer tubular shaft 718 may reduce or eliminate galling effects from the relative rotation between the two structures. In some instances, galling may generate dark or black materials that may pigment the pulverized material. This pigmentation may interfere with various analyses of the pulverized material, and/or the ability of the user to assess heat-related effects of the tissue removal device on the pulverized tissue. In one specific example, the outer tubular shaft 718 may comprise 304 stainless steel while the thread structure 724 may comprise 17-4 stainless steel. The thread structure 724 may be integrally formed with the inner shaft 722, e.g. grounded or formed from a base hypotube structure, but in other examples the thread structure 724 may be attached to the inner shaft 722 by welding, adhesives or other attachment processes. For example, the thread structure 724 may comprise a coiled stainless steel or Parylene wire that may be attached using epoxy along its entire length to the inner shaft 722 or may be attached at certain locations, e.g. the proximal end and the distal end of the thread structure 724. In some instances, partial attachment of the thread structure 724 to the shaft 722 may permit greater flexion or other deformation of that section of the tissue removal system 700 by permitting greater tensile or compressive strain in the thread structure 724 compared to the inner shaft 722. This greater flexion may also reduce heat generation between the thread structure 724 and inner shaft 722.

Figure 25:
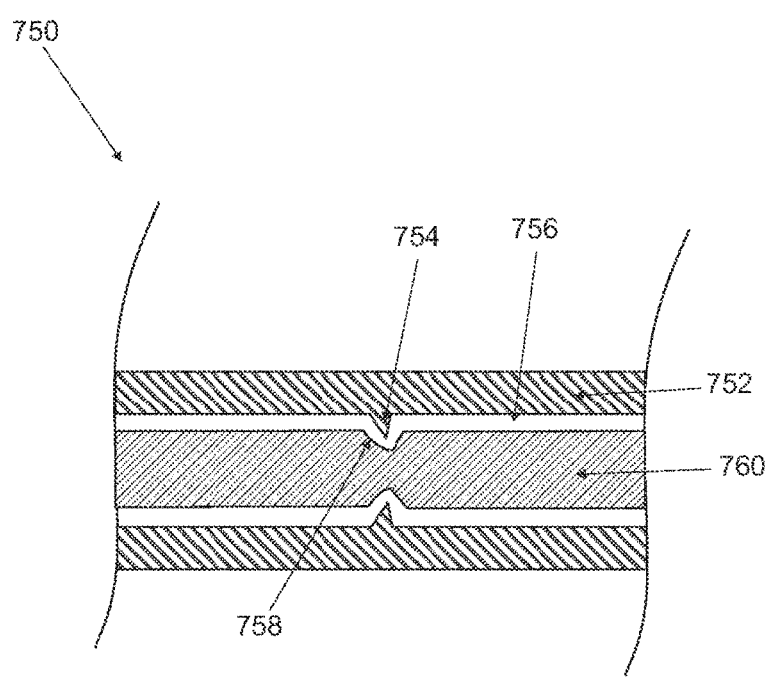
FIG. 25 schematically illustrates another embodiment of a cutting mechanism.

FIG. 25 schematically depicts another example of a cutting mechanism where instead of a cutting edge 720 located at the distal opening of the outer tubular shaft 718 as depicted in FIGS. 21A to 21D, the tissue removal system may comprise an internal cutting or grinding mechanism 750. This mechanism comprises an outer tubular shaft 752 with an inner cutting or grinding structure 754 that protrudes into the inner lumen 756 of the outer tubular shaft 752 and cooperates with a circumferential groove or recess 758 on the inner tubular shaft 760 to morcellize, cut or otherwise breakdown any larger tissue fragments that may enter the outer tubular shaft 752. The inner cutting structure 754 may have any of a variety of configurations, including different rake angles and/or surface configurations. The configuration of the recess 758 on the inner tubular shaft 760 may vary in width and cross-sectional shape. Although only a single internal mechanism 750 is depicted, in other examples, multiple mechanisms may be provided along the shafts 752 and 760. In some further examples, an internal mechanism 750 may be used with the tip-based mechanism illustrated in FIGS. 21A to 21D.

Figure 22:
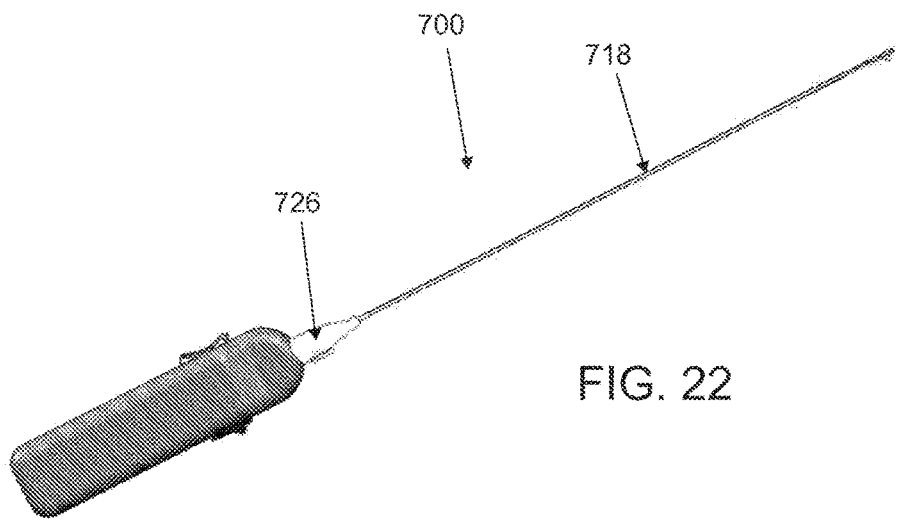
FIG. 22 illustrates the tissue removal device of FIG. 21A with an optional viewing chamber.
Figure 23:
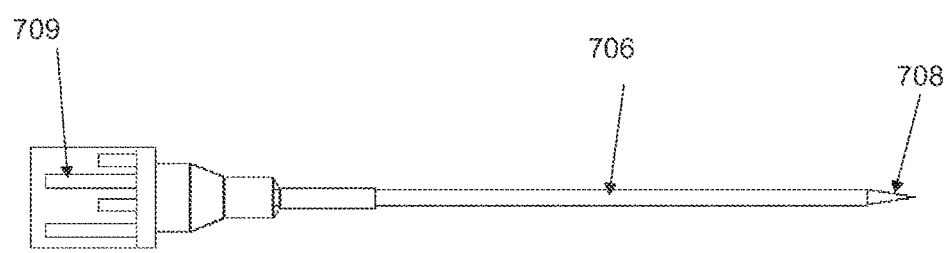
FIG. 23 illustrates an embodiment of a cannula and obturator device usable with various access systems.

FIG. 22 further depicts another optional feature of a tissue removal system 700, comprising an optically transparent chamber 726. Although the optically transparent chamber section 726 in FIG. 22 is located distally at the attachment of the outer tubular shaft 718, in other examples, the optically transparent housing chamber 726 may be located at a more proximal location. The optically transparent housing section 726 comprises an optically clear passageway or cavity in communication with the lumen of the outer tubular shaft 718 so that any fluid and/or materials either injected distally or removed proximally may be viewed by the user. In some instances, the passageway or cavity may have a volume of at least about 0.5 cc, sometimes about 1 cc, and other times about 2 cc or more. The optically transparent housing chamber 726 may also comprise markings to identify the volume of material that has aspirated or prepared for infusion or irrigation, for example. The optically transparent chamber 726 may also features a removable cap to empty the contents for of the chamber 726, to reduce clogging or to collect a diagnostic tissue sample. In some examples, the tissue removal system may have one or more infusion lumens with one or more openings at the base, cable shaft, and/or distal tip of the tissue removal system, which may be used in addition to or in lieu distal end of the outer tubular shaft 718. In other examples, the tissue removal system may be removed from the vertebral body and a separate infusion instrument may be used to deliver therapeutic agents or materials.

Figure 24A:
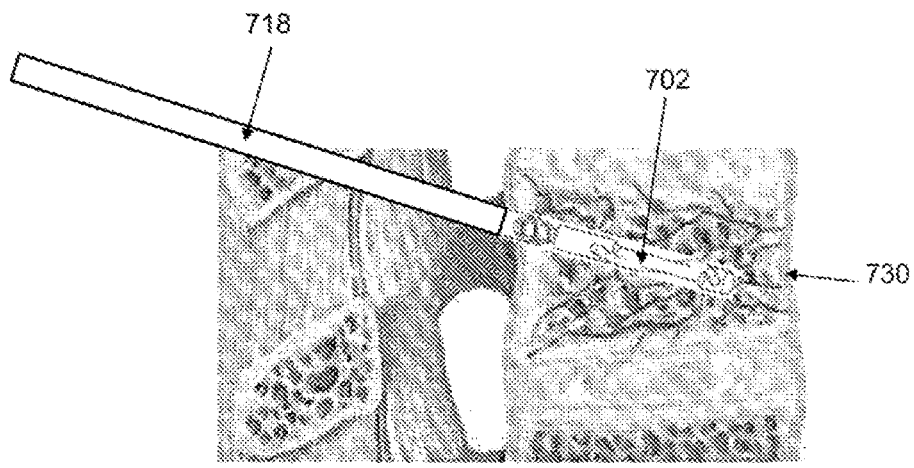
FIGS. 24A to 24C depicts one embodiment for performing vertebroplasty.
Figure 24B:
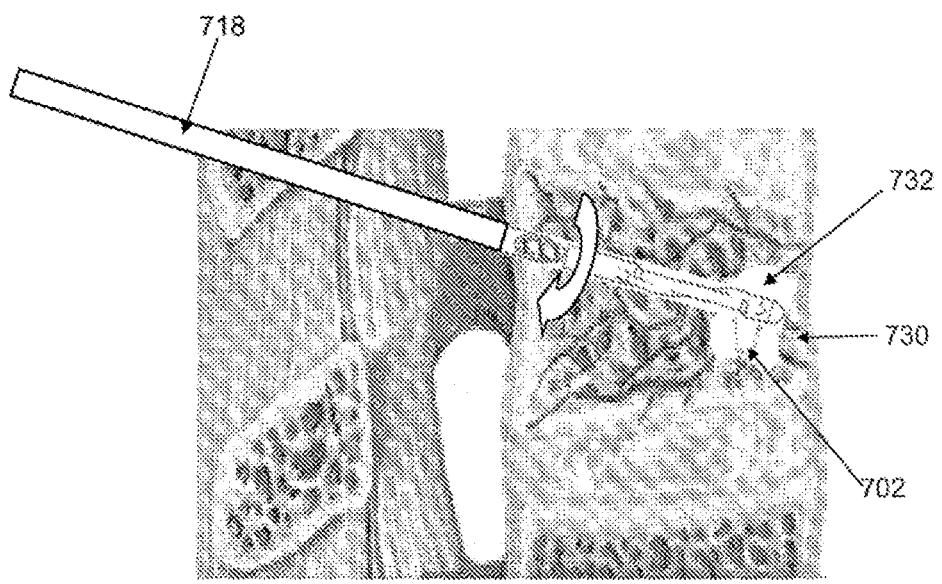
Figure 24C:
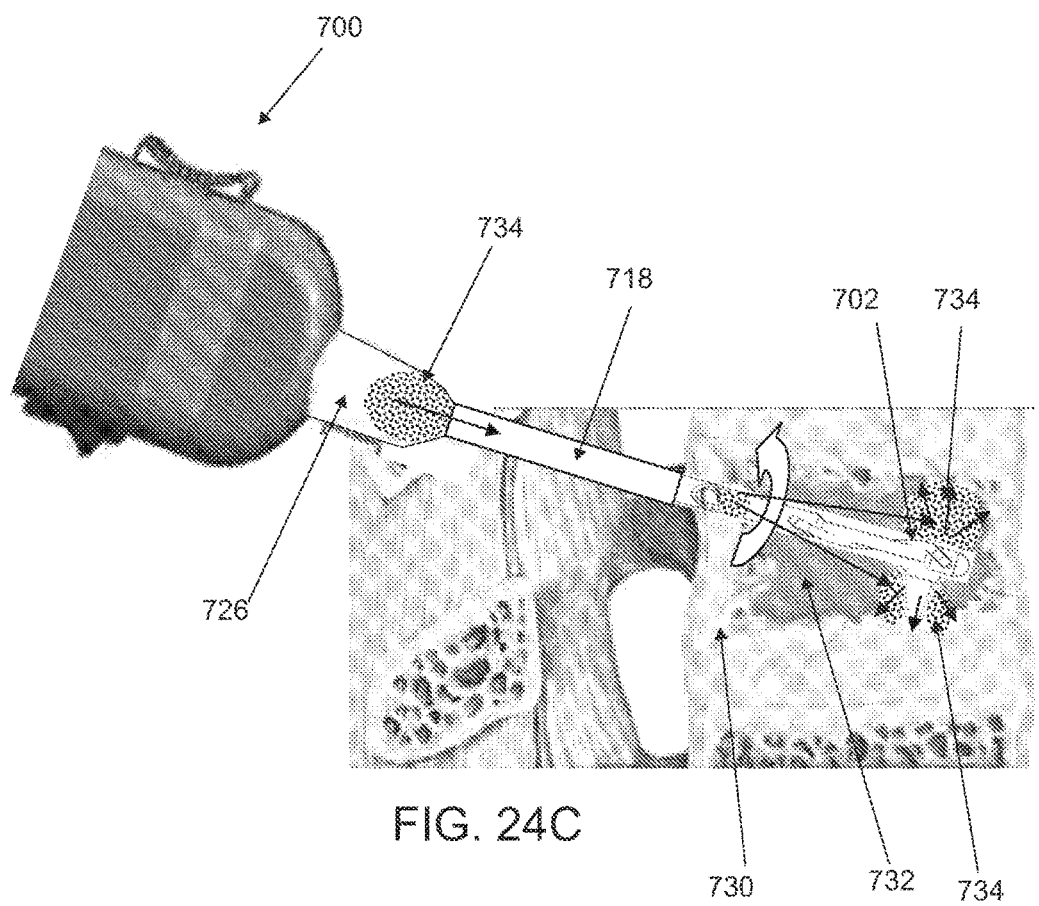

In use, the tissue removal system 700 depicted in FIGS. 21A to 22 may be used for any of a variety of tissue removal procedures, including discectomy and vertebroplasty, depending upon the particular configuration. Referring to FIGS. 24A and to 24C, a vertebral body 730 may be accessed by any of a variety of access procedures described herein. A tissue removal system 700 (with a shaft 718—not drawn to scale) may be inserted into the interior of the vertebral body (FIG. 24A) and then rotated with the cable 702 extended to form a cavity 732 in the vertebral body 730 (FIG. 24B). The tissue removal system 700 may be further manipulated until adequate removal of cancellous bone is achieved. As shown in FIG. 24C, the tissue removal system 700 may be loaded with a bone cement 734 which is then delivered to the cavity 732. In some examples, the bone cement 734 may comprise a material such as polymethyl methacrylate hydroxyapatite, or any of a variety of other bone cements or other hardenable or curable substances can be injected through the trocar to fill the cavity created by the by the tissue removal system 700. The cable 702 of the tissue removal system 700 may be retracted or extended during delivery of therapeutic agents. In some instances, the extended cable 702 may redistribute the therapeutic agents against the cavity walls, which may reduce the risk of leakage out of the cavity.

In some of the procedures described above, the cavity in the vertebral body is formed before the delivery of therapeutic agents, but in other procedures, the delivery of therapeutic agents may occur simultaneously. In procedure where the cavity is first formed, filling of the empty cavity may reduce initial filling pressures. In some instances, lower filling pressures may reduce the risk of leakage. In some examples, the tissue removal system may comprise a pressure sensor which may be used by the user or may be configured automatically to shut off delivery or pressurization of the therapeutic agents upon reaching a particular pressure limit.

Although some of the examples described herein are directed to treatment of vertebral disc fractures, in other examples, the tissue removal systems may be used to treat or diagnose bone lesions located in the vertebrae or other bones of the body. Diagnosis of bone lesions may include biopsy of bone. These bone lesions may include but are not limited to potentially cancerous bone lesions, including osteomas, osteosarcomas and metastatic lesions, as well as potentially infectious bone lesions, including tuberculosis. Bone cement, with or without other therapeutic agents such as anti-neoplastic and anti-infective agents, may or may not be injected into the It is to be understood that this invention is not limited to particular exemplary embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

What is claimed as new and desired to be protected by Letters Patent of the United States is:

1. A method for removing tissue at a target tissue region comprising:
    advancing a cannula to a target tissue region;
    advancing a tissue removal system through the cannula to a target tissue region, wherein the tissue removal system comprises a motor and a rotatable shaft assembly coupled to the motor, wherein the rotatable shaft assembly comprises: a shaft with a proximal opening along a side surface, a proximal groove adjacent to the proximal opening, a distal opening along a side surface, and a distal groove adjacent to the distal opening, wherein at least the distal grooves comprises an angular offset from a longitudinal axis of the shaft and the angular offset of the distal groove is greater than an angular offset, if any, of the proximal groove; a flexible elongate member coupled to the shaft through the proximal opening and the distal opening, wherein a proximal portion of the elongate member is at least partially seated within the proximal groove and the distal portion of the elongate member is at least partially seated within the distal groove, and the elongate member has a first retracted configuration and a second extended configuration, and wherein the tissue removal system is advanced with the elongate member in the first retracted configuration;
    transitioning the flexible elongate member to the second extended configuration;
    rotating the rotatable shaft assembly to cut the target tissue with the elongate member; and
    removing tissue from the target tissue region.

2. The method of claim 1, wherein removing tissue comprises transporting tissue along an inner shaft of the rotatable shaft assembly.

3. The method of claim 1, further comprising visualizing the target tissue region using an endoscope.

* * * * *